US008110680B2

(12) United States Patent
Maruoka et al.

(10) Patent No.: US 8,110,680 B2
(45) Date of Patent: Feb. 7, 2012

(54) OPTICALLY ACTIVE QUATERNARY AMMONIUM SALT HAVING AXIAL ASYMMETRY, AND METHOD FOR PRODUCING ALPHA-AMINO ACID AND DERIVATIVE THEREOF BY USING THE SAME

(75) Inventors: Keiji Maruoka, Kyoto (JP); Kenichiro Yamamoto, Hyogo (JP); Yukifumi Nishimoto, Hyogo (JP)

(73) Assignee: Nagase & Co., Ltd., Osaka-shi (JP)

( * ) Notice: Subject to any disclaimer, the term of this patent is extended or adjusted under 35 U.S.C. 154(b) by 0 days.

(21) Appl. No.: 12/443,588

(22) PCT Filed: Sep. 13, 2007

(86) PCT No.: PCT/JP2007/068332
§ 371 (c)(1),
(2), (4) Date: Mar. 30, 2009

(87) PCT Pub. No.: WO2008/038578
PCT Pub. Date: Apr. 3, 2008

(65) Prior Publication Data
US 2010/0029935 A1    Feb. 4, 2010

(30) Foreign Application Priority Data

Sep. 28, 2006 (JP) .................................. 2006-265618

(51) Int. Cl.
*C07D 223/18* (2006.01)
(52) U.S. Cl. ........................................................ 540/587
(58) Field of Classification Search ................... 540/587
See application file for complete search history.

(56) References Cited

U.S. PATENT DOCUMENTS

| 6,340,753 | B1 | 1/2002 | Maruoka |
| 2006/0183896 | A1 | 8/2006 | Maruoka |
| 2007/0135654 | A1 | 6/2007 | Maruoka |
| 2007/0161624 | A1 | 7/2007 | Maruoka |
| 2009/0054679 | A1 | 2/2009 | Maruoka et al. |
| 2009/0270614 | A1 | 10/2009 | Maruoka et al. |

FOREIGN PATENT DOCUMENTS

| EP | 1 854 796 A1 | 11/2007 |
| EP | 1 870 403 A8 | 12/2007 |
| JP | 2001-48866 | 2/2001 |
| JP | 2002-173492 | 6/2002 |
| JP | 2002-326992 | 11/2002 |
| JP | 2003-81976 | 3/2003 |
| JP | 2004-189696 | 7/2004 |
| JP | 2004-238362 | 8/2004 |
| JP | 2004-359578 | 12/2004 |
| JP | 2005-41791 | 2/2005 |
| WO | WO 2006/054366 | 5/2006 |
| WO | WO 2006/093269 A1 | 9/2006 |
| WO | WO 2006/104226 A1 | 10/2006 |

OTHER PUBLICATIONS

Takashi Ooi, et al., "Design of N-Spiro $C_2$-Symmetric Chiral Quarternary Ammonium Bromides as Novel Chiral Phase-Transfer Catalysts: Synthesis and Application to Practical Asymmetric Synthesis of α-Amino Acids", J. Am. Chem. Soc., 2003, vol. 125, pp. 5139-5151.

Bruno Bellier, et al., "Synthesis and Biological Properties of New Constrained CCK-B Antagonists: Discrimination of Two Affinity States of the CCK-B Receptor on Transfected CHO Cells", Journal of Medicinal Chemistry, vol. 40, No. 24, 1997, pp. 3947-3956.

Eric Mossel, et al., "Aspartame dipeptide analogues: effect of number of side-chain methylene group spacers and Cα-methylation in the second position", Tetrahedron Asymmetry, vol. 8, No. 8, 1997, pp. 1305-1314.

Takayuki Shioiri, et al., "Asymmetric Phase Transfer Catalysis", Stimulating Concepts in Chemistry, 2000, p. 123.

Martin J. O'Donnell, "The Preparation of Optically Active α-Amino Acids from the Benzophenone Imines of Glycine Derivatives", Aldrichimica Acta, vol. 34, No. 1, 2001, 13 Pages.

Takashi Ooi, et al., "Practical Catalytic Enantioselective Synthesis of α, α-Dialkyl- α-amino Acids by Chiral Phase-Transfer Catalysis", J. Am. Chem. Soc., vol. 122, No. 21, 2000, 5 Pages.

Joan M. Insole, "Steric Effects of Methoxy-groups in 2,2'-Bridged Biphenyls. Part II [1]", Perkin Transactions 2: Physical Organic Chemistry, No. 9, 1972, pp. 1168-1173.

G. H. Beaven, et al., "Relation between configuration and conjugation in diphenyl derivatives. I. The enantiomorphism and ultraviolet absorption spectra of some 2, 2' bridged compounds", Chemical Abstracts, Journal of the Chemical Society, vol. 46, 67079, OREF 46, 1952, pp. 11211e-l, 11212 a-i.

Zhenfu Han, et al., "Convenient preparation of highly active phase-transfer catalyst for catalytic asymmetric synthesis of α-alkyl- and α, α-dialkyl- α-amino acids: application to the short asymmetric synthesis of BIRT-377", Tetrahedron Letters, vol. 46, No. 49, 2005, pp. 8555-8558.

Barry Lygo, et al., "Identification of a highly effective asymmetric phase-transfer catalyst derived from α-methylnaphthylamine", Tetrahedron Letters, vol. 44, No. 30, 2003, pp. 5629-5632.

Takashi Ooi, et al., "Molecular Design of a $C_2$-Symmetric Chiral Phase-Transfer Catalyst for Practical Asymmetric Synthesis of α-Amino Acids", Journal of American Chemical Society, vol. 121, No. 27, 1999, pp. 6519-6520.

A. M. Costero, et al., Anales de Quimica, vol. 89, No. 1, 1993, pp. 95-98.

(Continued)

*Primary Examiner* — Brenda Coleman
(74) *Attorney, Agent, or Firm* — Oblon, Spivak, McClelland, Maier & Neustadt, L.L.P.

(57) ABSTRACT

The present invention discloses an optically active quarternary ammonium salt having axial asymmetry and a method for producing an α-amino acid and a derivative thereof using the same. The optically active quaternary ammonium salt having axial asymmetry of the present invention is a chiral phase-transfer catalyst that has a simple structure and that can be produced in a smaller number of process steps. The compound of the present invention is very useful as a phase-transfer catalyst in the synthesis of an α-alkyl-α-amino acid and a derivative thereof as well as an α,α-dialkyl-α-amino acid and a derivative thereof. Therefore, the compound of the present invention can be used in the development of novel foods and pharmaceuticals.

4 Claims, No Drawings

OTHER PUBLICATIONS

Yong-Gang Wang, et al., "Convenient preparation of chiral phase-transfer catalysts with conformationally fixed biphenyl core for catalytic asymmetric synthesis of α-alkyl- and α, α-dialkyl- α-amino acids: application to the short asymmetric synthesis of BIRT-377", Tetrahedron, vol. 63, No. 26, 2007, pp. 6042-6050.

Yong-Gang Wang, et al., "Design of Chiral Phase Transfer Catalyst with Conformationally Fixed Biphenyl Core: Application of Asymmetric Alkylation of Glycine Derivatives", Organic Process Research & Development, vol. 11, No. 3, 2007, pp. 628-632.

Andrew P. Abbott, et al., "Electrochemical recognition of analytes using quaternary ammonium binaphthyl salts", Database CA [Online], Chemical Abstracts Service, XP002532001, Database accession No. 2003:168090.

Donald D. Fitts, et al., "Configurational studies in the biphenyl series. IV. Conformation and optical rotation of restricted biphenyls. Configurational correlation of biaryls by optical displacement. The absolute configuration of restricted 1,1'-binaphthyls", Database CA [Online], Chemical Abstracts Service, XP002532002, Database accession No. 1958 : 55790.

Shi Min, et al., "Synthesis of axially dissymmetric chiral ammonium salts by quaternization of secondary amines with (R)-(+)-2,2'-bis (bromomethyl)-6,6' -dinitro biphenyl and (R)-(+)-2,2' -bis (bromomethyl)-1,1' -binaphthyl and an examination of their abilities as chiral phase-transfer catalysts", Database CA [Online}, Chemical Abstracts Service, XP002532003, retrieved from STN, Database accession No. 1995:419364, 1995.

Database Crossfire Beilstein, Beilstein Institut Zur Foerderung Der Chemischen Wissenchaften, Database accession No. 4927823, XP002532004, 1955.

Otto Th. Schmidt, et al., "Optisch Aktive 2, 3, 4, 2', 3', 4'-Hexamethoxy-Diphenyldicarbonsaure-6, 6' XIII. Mitteilung Über Natürliche Gerbstoffe", Ann Chem. vol. 576, No. 85, Feb. 18, 1952, pp. 85-93 (English translation of p. 87, line 14 to end of p. 89).

Andrew P. Abbott, et al., "Electrochemical recognition of charged species using quaternary ammonium binaphthyl salts", Analyst, vol. 126, 2001, 1892-1896.

Frédéric Cottineau, et al., "Reductive Cleavage of Axially Disymmetric Tertiary Amines and Quaternary Ammonium Salts by Lithium Aluminium Hydride. Synthesis of New 1,1'-Binaphthyl Substituted Amines", Tetrahedron Letters, vol. 26, No. 4, 1985, pp. 421-424.

Lorenzo Di Bari, et al., "Conformational Study of 2,2'-Homosubstituted 1,1'-Binaphthyls by Means of UV and CD Spectroscopy", J. Am. Chem. Soc., vol. 121, 1999, pp. 7998-8004.

Masaya Ikunaka, et al., "A Scalable Synthesis of (R)-3,5-Dihydro-4H-dinaphth[2,1-c:1'2'-e]azepine" Organic Process Research & Development, vol. 7, 2003, pp. 644-648.

S. F. Mason, et al., "Optical Activity in the Biaryl Series", Tetrahedron, vol. 30, 1974, pp. 1671-1682.

Takashi Ooi, et al., "New, Improved Procedure for the Synthesis of Structurally Diverse N-Spiro C2-Symmetric Chiral Quaternary Ammonium Bromides", J. Org. Chem., vol. 68, 2003, pp. 4576-4578.

Masahiko Seki, et al., "A Practical Synthesis of C2-Symmetric Chiral Binaphthyl Ketone Catalyst", Synthesis, No. 12, 2000, pp. 1677-1680.

Irena G. Stará, et al., "Nucleophilic Cleavage of 4,5-Dihydro-3H-dinaphth[2,1-c:1',2'-e]azepinium Quaternary Salts. A Convenient Approach to New Axially Dissymmetric and Axially Asymmetric Ligands", J. Org. Chem., vol. 57, 1992, pp. 6966-6969.

Irena G. Stará, et al., "Optically Pure (S)- and (R)-4,5-Dihydro-3H-4-Methyldinaphth[2,1-c;1',2'-e]Azepines. Application to the Synthesis of new Bidentate Ligands with Axial Asymmetry", Tetrahedron: Asymmetry, vol. 3, No. 11, 1992, pp. 1365-1368.

Irena G. Stará, et al., "Stereochemical Dichotomy in the Stevens Rearrangement of Axially Twisted Dihydroazepinium and Dihydrothiepinium Salts. A Novel Enantioselective Synthesis of Pentahelicene", J. Am. Chem. Soc., vol. 116, 1994, pp. 5084-5088.

Irena G. Stará, et al., "Nucleophilic Attack on 4,5-Dihydro-4-alkyl-3H-dinaphtho[2,1-c:1',2'-e]thiepinium Salts. A Convenient Approach to New 2,2'-Bidentate 1,1'-Binaphthalene Ligands with Sulfur Donor Atoms", J. Org. Chem., vol. 59, 1994, pp. 1326-1332.

Taichi Kano, et al., "Design of new polyamine-based chrial phase-transfer catalysts for the enantioselective synthesis of phenylalanine", Tetrahedron: Asymmetry, vol. 15, 2004, pp. 1243-1245.

Masanori Kitamura, et al., "Powerful Chiral Phase-Transfer Catalysts for the Asymmetric Synthesis of α-Alkyl- and α, α-Dialkyl-α-amino Acids", Angewandte Chemie, vol. 44, 2005, pp. 1549-1551.

Yoshiki Kashiwada, et al., "New Hexahydroxybiphenyl Derivatives as Inhibitors of Protein Kinase C", J. Med. Chem., vol. 37, No. 1, 1994, pp. 195-200.

Takashi Ooi, et al., "A New N-Spiro C2-Symmetric Chiral Quaternary Ammonium Bromide Consisting of 4,6-Disubstituted Biphenyl Subunit as an Efficient Chiral Phase-Transfer Catalyst", Synlett, No. 12, 2003, pp. 1931-1933.

J.D. Reitze, et al., "The Further Chemistry of Ellagic Acid I. Synthesis of Tetramethylellagic Acid and Associated Polymer Precursors1)", Holzforschung, vol. 55, No. 2, 2001, pp. 171-175.

Yuri N. Belokon, et al., "Copper(II)salen catalysed, asymmetric synthesis of α,α-disubstituted amino acids", Tetrahedron, vol. 60, 2004, 1849-1861.

Jin-Tai Chen, et al., "Synthesis of D-Phenylalanine Using Chiral Phase-Transfer Catalyst", Youji Huaxue, vol. 8, 1988, pp. 164-166 (with English Abstract and an additional page).

Keiji Maruoka, et al., "Enantioselective Amino Acid Synthesis by Chiral Phase-Transfer Catalysis", Chem. Rev., vol. 103, 2003, pp. 3013-3028.

P. Bey, et al., "Synthesis of α-Alkyl and α-Functionalized Methyl-α-Amino Acids", Tetrahedron Letters, No. 17, 1977, pp. 1455-1458.

Martin J. O'Donnell, et al., "The Stereoselective Synthesis of α-Amino Acids by Phase-Transfer Catalysis", J. Am. Chem. Soc., vol. 111, 1989, pp. 2353-2355.

Hyeung-geun Park, et al., "Highly Enantioselective Phase-Transfer Catalytic Alkylation in the Preparation of Non-natural α-Amino Acids via Solid Phase Synthesis Using Aldimine Linker", J. Org. Chem., vol. 70, 2005, pp. 1904-1906.

Yuichiro Arimura, et al., "Highly Enantioselective Monoalkylation of Aldimine Schiff Base of Glycine Ester by Designer Chiral Phase-Transfer Catalysts", The Chemical Society of Japan, Dai 86 Shunki Nenkai (2006), Koen Yokoshu II, 2 H5-44, Mar. 13, 2006, p. 1073 (with partial English Translation).

Shakti R. Ahmed, et al., "Steric effects in 2,2'-bridged biphenyls with a heterocyclic bridging ring. I. Optically active dihydrodibenzazepines", Chemical Abstract 53:2119 OREF 53: 405C-I, 406A, Journal of the Chemical Society, 1958, pp. 3043-3047.

Shakti R. Ahmed, et al., "Steric effects in 2,2'-bridged biphenyls with a heterocyclic bridging ring. III. Ultraviolet absorption spectra of some dihydrodibenzazepinium compounds.", Chemical Abstract 55:38083, OREF 55: 7430c-f, Journal of the Chemical Society, 1960, pp. 4165-4169.

U.S. Appl. No. 13/039,645, filed Mar. 3, 2011, Maruoka.

OPTICALLY ACTIVE QUATERNARY AMMONIUM SALT HAVING AXIAL ASYMMETRY, AND METHOD FOR PRODUCING ALPHA-AMINO ACID AND DERIVATIVE THEREOF BY USING THE SAME

CROSS-REFERENCE TO RELATED APPLICATIONS

This application is a 371 of PCT/JP07/68332 filed Sep. 13, 2007 and claims the benefit of JP2006-265618 filed Sep. 28, 2006.

TECHNICAL FIELD

The present invention relates to an optically active quaternary ammonium salt having axial asymmetry and a method for producing the same. The present invention further relates to a method for producing an optically active α-amino acid and derivatives thereof by using this optically active quaternary ammonium salt having axial asymmetry as a phase-transfer catalyst.

BACKGROUND ART

α-Alkyl-α-amino acids represented by the formula $H_2NCH(R)COOH$ are very important naturally-occurring α-amino acids. α-Alkyl-α-amino acids in which the α-carbon has an L-configuration are a structural component of proteins (polypeptide chains) that exist in animals, plants, and microorganisms, for example. The D-form of α-alkyl-α-amino acids exists in plants, fungi and microorganisms as a structural component of non-proteogenic compounds. On the other hand, α,α-dialkyl-α-amino acids are recently gaining attention because of their unique functions, including the fact that they are stereochemically stable and that when they are incorporated into peptides, those peptides are not susceptible to enzymatic hydrolysis by proteases (see Bellier, B. et al. (1997). *J. Med. Chem.* 40:3947 and Mossel, E. et al. (1997). *Tetrahedron Asymmetry* 8:1305). These properties have led α,α-dialkyl-α-amino acids to be considered for use as chiral building blocks for the synthesis of peptides having enhanced activity, effective enzyme inhibitors, and compounds having other various biological activities. Methods for synthesizing non-proteogenic α-amino acids, particularly α,α-dialkyl-α-amino acids, by selectively building the stereochemistry of the α-carbon have been investigated, but at the present time, a practical method has not yet been found.

Chiral phase-transfer catalysts that allow stereoselective alkylation of glycine derivatives are easy to use and can be applied widely, and thus have become increasingly important in the field of process chemistry. A large amount of research into designing phase-transfer catalysts has been conducted mainly by using cinchona alkaloid derivatives, and to date several useful methods have been reported (e.g., see Shioiri, T. et al., Stimulating Concepts in Chemistry, edited by Vogtle, F. et al., WILEY-VCH: Weinheim, p. 123, 2000; and O'Donnell, M. J. (2001). *Aldrichimica Acta*, 34:3). However, when such phase-transfer catalysts are used in a reaction, various problems are caused, including the fact that halogen-based solvents are employed, the reaction is sluggish, and low temperature conditions are required. In particular, the use of chiral phase-transfer catalysts derived from such cinchona alkaloids is not particularly efficient in the synthesis of α,α-dialkyl-α-amino acids.

The present inventors have prepared an optically active quaternary ammonium salt having axial asymmetry, and have clearly shown that it can be used as a phase-transfer catalyst for stereoselectively synthesizing α-alkyl-α-amino acids and α,α-dialkyl-α-amino acids (see Japanese Laid-Open Patent Publication Nos. 2001-48866 and 2003-81976; and Ooi, T. et al. (2000). *J. Am. Chem. Soc.* 122:5228). For example, a spiro-compound represented by the following formula is very effective for stereoselectively producing α,α-dialkyl-α-amino acids because it catalyzes the stereoselective double alkylation of glycine derivatives and the stereoselective monoalkylation of α-alkyl-α-amino acid derivatives:

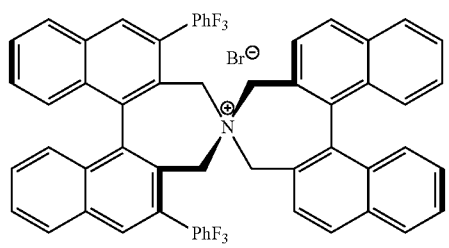

(where $PhF_3$ represents a 3,4,5-trifluorophenyl group). However, the preparation of such spiro-type catalysts requires many process steps; for example, if chiral binaphthol, which is easily available, is used as the starting material, then eleven process steps are required just to prepare the portion represented by the left half of the chemical structure formula of the catalyst. Therefore, it has been pointed out that preparation of conventional optically active quaternary ammonium salts having axial asymmetry may be extremely time-consuming and costly.

DISCLOSURE OF INVENTION

It is an object of the present invention to provide a chiral phase-transfer catalyst that has a simple structure and that can be produced in a smaller number of process steps.

The present invention provides a compound represented by Formula (I) below:

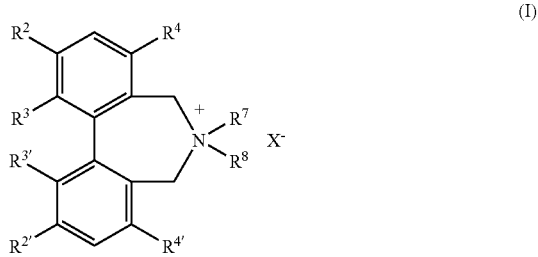

wherein
$R^2$ and $R^{2'}$ are each independently:
  a hydrogen atom; or
  an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and
a halogen atom;

$R^3$ and $R^{3'}$ are each independently:
a $C_1$ to $C_5$ alkoxy group that may be substituted with a halogen atom and/or an aryl group, and/or that may be branched or form a cyclic group;

$R^4$ and $R^{4'}$ are each independently a group selected from the group consisting of:
(i) a hydrogen atom;
(ii) a halogen atom;
(iii) a $C_1$ to $C_6$ alkyl group that may be branched or form a cyclic group and that may be substituted with a halogen atom;
(iv) a $C_2$ to $C_6$ alkenyl group that may be branched or form a cyclic group and that may be substituted with a halogen atom;
(v) a $C_2$ to $C_6$ alkynyl group that may be branched or form a cyclic group and that may be substituted with a halogen atom;
(vi) an aralkyl group, wherein the aryl moiety constituting the aralkyl group may be substituted with at least one group selected from the group consisting of:
  a $C_1$ to $C_4$ alkyl group that may be branched and that may be substituted with a halogen atom,
  a $C_1$ to $C_5$ alkoxy group that may be branched and that may be substituted with a halogen atom,
  an aryl group that may be substituted with a halogen atom or a $C_1$ to $C_4$ alkyl group that may be branched and that may be substituted with a halogen atom, and
  a halogen atom; and
(vii) an aryl group, wherein the aryl group may be substituted with at least one group selected from the group consisting of:
  a $C_1$ to $C_4$ alkyl group that may be branched and that may be substituted with a halogen atom,
  a $C_1$ to $C_5$ alkoxy group that may be branched and that may be substituted with a halogen atom,
  an aryl group that may be substituted with a halogen atom or a $C_1$ to $C_4$ alkyl group that may be branched and that may be substituted with a halogen atom, and
  a halogen atom;

$R^7$ and $R^8$ are each independently a group selected from the group consisting of:
(i) a $C_1$ to $C_{30}$ alkyl group that may be branched or form a cyclic group and that may be substituted with a halogen atom;
(ii) a $C_2$ to $C_{12}$ alkenyl group that may be branched or form a cyclic group and that may be substituted with a halogen atom;
(iii) a $C_2$ to $C_{12}$ alkynyl group that may be branched or form a cyclic group and that may be substituted with a halogen atom; and
(iv) an aryl group, wherein the aryl group may be substituted with at least one group selected from the group consisting of:
  a $C_1$ to $C_4$ alkyl group that may be branched and that may be substituted with a halogen atom,
  a $C_1$ to $C_5$ alkoxy group that may be branched and that may be substituted with a halogen atom,
  an aryl group that may be substituted with a halogen atom or a $C_1$ to $C_4$ alkyl group that may be branched and that may be substituted with a halogen atom, and
  a halogen atom; or $R^7$ and $R^8$ are taken together to form a divalent group selected from the group consisting of:
—$(CH_2)_m$— (where m is an integer from 2 to 8);

[chemical structures: tetralin-like bicyclic; crown ether-like ring with four O atoms; tetrahydropyran; thiane (S-containing ring); N-phenylpiperidine; piperidine-N-C(=O)-O-C(CH$_3$)$_2$-CH$_3$; and a dibenzo-fused seven-membered ring with substituents $R^{27}$, $R^{28}$, $R^{29}$, $R^{32}$, $R^{33}$, $R^{34}$]

(where $R^{27}$, $R^{28}$, $R^{29}$, $R^{32}$, $R^{33}$ and $R^{34}$ are each independently a group selected from the group consisting of:
a hydrogen atom;
a $C_1$ to $C_8$ alkyl group that may be branched or form a cyclic group, and/or that may be substituted with a halogen atom;
a $C_2$ to $C_8$ alkenyl group that may be branched or form a cyclic group, and/or that may be substituted with a halogen atom;
a $C_2$ to $C_8$ alkynyl group that may be branched or form a cyclic group, and/or that may be substituted with a halogen atom;
an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group; and
an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group), and $X^-$ is an anion selected from the group consisting of a halide anion, $SCN^-$, $HSO_4^-$, $HF_2^-$, $CF_3SO_3^-$, $CH_3$—$C_6H_4$—$SO_3^-$, and $CH_3SO_3^-$.

In one embodiment, $R^2$ and $R^{2'}$ of the compound represented by Formula (I) are both hydrogen atoms.

In one embodiment, $R^2$ and $R^{2'}$ of the compound represented by Formula (I) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

In one embodiment, $R^4$ and $R^{4'}$ of the compound represented by Formula (I) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

The present invention also provides a method for producing the compound represented by Formula (I) described above, the method comprising:

a step of reacting a compound represented by Formula (II) below:

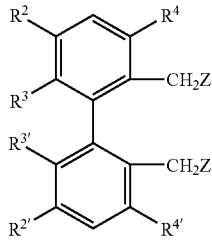

(II)

with a secondary amine represented by Formula (III) below:

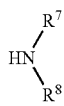

(III)

in an organic solvent in the presence of an acid-scavenging agent, wherein in Formula (II), $R^2$ and $R^{2'}$ are each independently:

a hydrogen atom; or an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom;

$R^3$ and $R^{3'}$ are each independently:

a $C_1$ to $C_5$ alkoxy group that may be substituted with a halogen atom and/or an aryl group, and/or that may be branched or form a cyclic group;

$R^4$ and $R^{4'}$ are each independently a group selected from the group consisting of:

(i) a hydrogen atom;

(ii) a halogen atom;

(iii) a $C_1$ to $C_6$ alkyl group that may be branched or form a cyclic group and that may be substituted with a halogen atom;

(iv) a $C_2$ to $C_6$ alkenyl group that may be branched or form a cyclic group and that may be substituted with a halogen atom;

(v) a $C_2$ to $C_6$ alkynyl group that may be branched or form a cyclic group and that may be substituted with a halogen atom;

(vi) an aralkyl group, wherein the aryl moiety constituting the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and (vii) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom, and Z is a halogen atom, and in Formula (III), $R^7$ and $R^8$ are each independently a group selected from the group consisting of:

(i) a $C_1$ to $C_{30}$ alkyl group that may be branched or form a cyclic group and that may be substituted with a halogen atom;

(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom; and (iv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; or $R^7$ and $R^8$ are taken together to form a divalent group selected from the group consisting of:

—$(CH_2)_m$— (where m is an integer from 2 to 8);

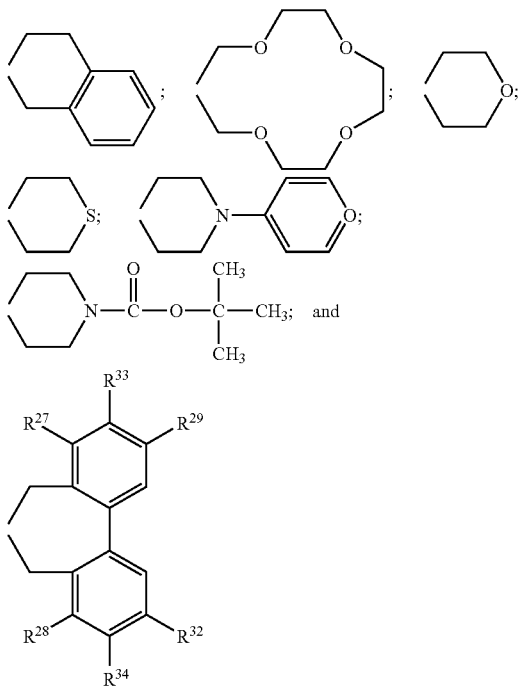

(where $R^{27}$, $R^{28}$, $R^{29}$, $R^{32}$, $R^{33}$ and $R^{34}$ are each independently a group selected from the group consisting of:
a hydrogen atom;
a $C_1$ to $C_8$ alkyl group that may be branched or form a cyclic group, and/or that may be substituted with a halogen atom;
a $C_2$ to $C_8$ alkenyl group that may be branched or form a cyclic group, and/or that may be substituted with a halogen atom;
a $C_2$ to $C_8$ alkynyl group that may be branched or form a cyclic group, and/or that may be substituted with a halogen atom;
an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group; and
an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group).

In one embodiment, $R^2$ and $R^{2'}$ of the compound represented by Formula (II) are both hydrogen atoms.

In one embodiment, $R^2$ and $R^{2'}$ of the compound represented by Formula (II) are both aryl groups, wherein the aryl group may be substituted with at least one group selected from the group consisting of:

a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom or a $C_1$ to $C_4$ alkyl group that may be branched and that may be substituted with a halogen atom, and
a halogen atom.

In one embodiment, $R^4$ and $R^{4'}$ of the compound represented by Formula (II) are both aryl groups, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom or a $C_1$ to $C_4$ alkyl group that may be branched and that may be substituted with a halogen atom, and
a halogen atom.

The present invention further provides a compound represented by Formula (II) below:

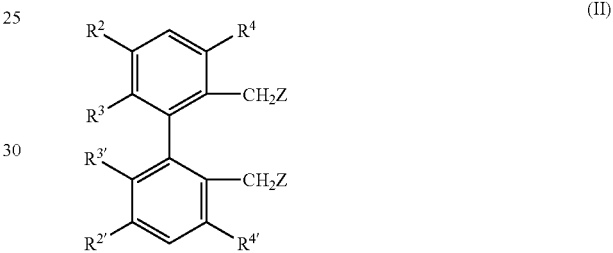

(II)

wherein
$R^2$ and $R^{2'}$ are each independently:
  a hydrogen atom; or
  an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom or a $C_1$ to $C_4$ alkyl group that may be branched and that may be substituted with a halogen atom, and
    a halogen atom;
$R^3$ and $R^{3'}$ are each independently:
  a $C_1$ to $C_5$ alkoxy group that may be substituted with a halogen atom and/or an aryl group, and/or that may be branched or form a cyclic group;
$R^4$ and $R^{4'}$ are each independently a group selected from the group consisting of:
  (i) a hydrogen atom;
  (ii) a halogen atom;
  (iii) a $C_1$ to $C_6$ alkyl group that may be branched or form a cyclic group and that may be substituted with a halogen atom;
  (iv) a $C_2$ to $C_6$ alkenyl group that may be branched or form a cyclic group and that may be substituted with a halogen atom;
  (v) a $C_2$ to $C_6$ alkynyl group that may be branched or form a cyclic group and that may be substituted with a halogen atom;
  (vi) an aralkyl group, wherein the aryl moiety constituting the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and (vii) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and Z is a halogen atom.

The present invention also provides a compound represented by Formula (VII) below:

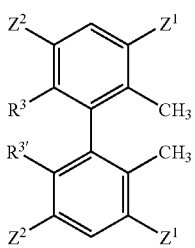

(VII)

wherein
$R^3$ and $R^{3'}$ are each independently:
a $C_1$ to $C_5$ alkoxy group that may be substituted with a halogen atom and/or an aryl group, and/or that may be branched or form a cyclic group;
$Z^1$ is a halogen atom; and
$Z^2$ is a hydrogen atom or a halogen atom.

The present invention further provides a method for stereoselectively producing a compound represented by Formula (VI):

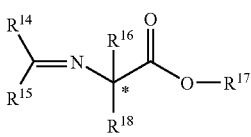

(VI)

the method comprising:
a step of alkylating a compound represented by Formula (IV):

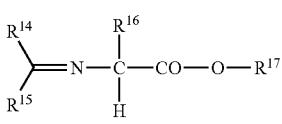

(IV)

with a compound of Formula (V):

$R^{18}$—W (V)

using a compound represented by Formula (I) that is pure with respect to its axial asymmetry as a phase-transfer catalyst:

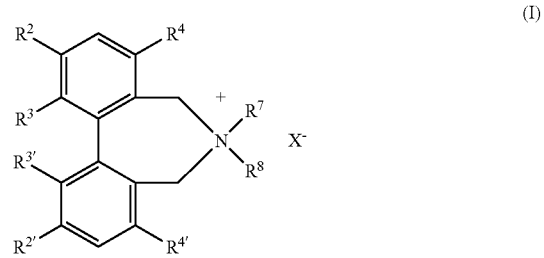

(I)

in a medium in the presence of an inorganic base,
wherein in Formula (I),
$R^2$ and $R^{2'}$ are each independently:
a hydrogen atom; or
an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom or a $C_1$ to $C_4$ alkyl group that may be branched and that may be substituted with a halogen atom, and
a halogen atom;
$R^3$ and $R^{3'}$ are each independently:
a $C_1$ to $C_5$ alkoxy group that may be substituted with a halogen atom and/or an aryl group, and/or that may be branched or form a cyclic group;
$R^4$ and $R^{4'}$ are each independently a group selected from the group consisting of:
(i) a hydrogen atom;
(ii) a halogen atom;
(iii) a $C_1$ to $C_6$ alkyl group that may be branched or form a cyclic group and that may be substituted with a halogen atom;
(iv) a $C_2$ to $C_6$ alkenyl group that may be branched or form a cyclic group and that may be substituted with a halogen atom;
(v) a $C_2$ to $C_6$ alkynyl group that may be branched or form a cyclic group and that may be substituted with a halogen atom;
(vi) an aralkyl group, wherein the aryl moiety constituting the aralkyl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom or a $C_1$ to $C_4$ alkyl group that may be branched and that may be substituted with a halogen atom, and
a halogen atom; and
(vii) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom;

$R^7$ and $R^8$ are each independently a monovalent organic group, or $R^7$ and $R^8$ are taken together to form a divalent organic group, and $X^-$ is a halide anion;

in Formulae (IV) and (VI), $R^{14}$ and $R^{15}$ are each independently:

(i) a hydrogen atom; or (ii) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom, with the proviso that a case where $R^{14}$ and $R^{15}$ are both hydrogen atoms is excluded;

$R^{16}$ is a group selected from the group consisting of:

(i) a hydrogen atom;

(ii) a $C_1$ to $C_{10}$ alkyl group that may be branched or form a cyclic group and that may be substituted with a halogen atom, wherein the alkyl group may be substituted with a $C_1$ to $C_5$ alkoxy group that may be branched and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety constituting the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and (vi) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and $R^{17}$ is a $C_1$ to $C_8$ alkyl group that may be branched or form a cyclic group, in Formulae (V) and (VI), $R^{18}$ is a group selected from the group consisting of:

(i) a $C_1$ to $C_{10}$ alkyl group that may be branched or form a cyclic group and that may be substituted with a halogen atom, wherein the alkyl group may be substituted with a $C_1$ to $C_5$ alkoxy group that may be branched and that may be substituted with a halogen atom;

(ii) a $C_2$ to $C_6$ alkenyl group that may be branched or form a cyclic group and that may be substituted with a halogen atom;

(iii) a $C_2$ to $C_6$ alkynyl group that may be branched or form a cyclic group and that may be substituted with a halogen atom;

(iv) an aralkyl group, wherein the aryl moiety constituting the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and (v) a $C_3$ to $C_9$ propargyl group or substituted propargyl group that may be branched and that may be substituted with a halogen atom, in Formula (V), W is a functional group having a leaving ability, and in Formula (VI),

* indicates a newly produced asymmetric center.

In one embodiment, $R^7$ and $R^8$ of the compound represented by Formula (I) are each independently a group selected from the group consisting of:

(i) a $C_1$ to $C_{30}$ alkyl group that may be branched or form a cyclic group and that may be substituted with a halogen atom;

(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom; and (iv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; or $R^7$ and $R^8$ are taken together to form a divalent group selected from the group consisting of:

—$(CH_2)_m$— (where m is an integer from 2 to 8);

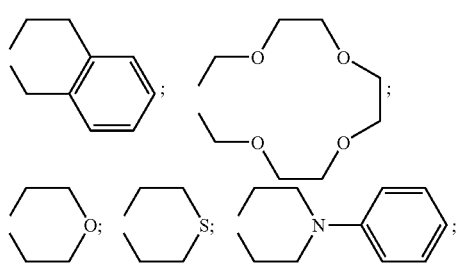

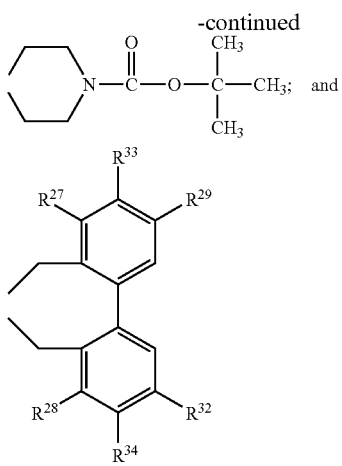

(where $R^{27}$, $R^{28}$, $R^{29}$, $R^{32}$, $R^{33}$ and $R^{34}$ are each independently a group selected from the group consisting of:

a hydrogen atom;

a $C_1$ to $C_8$ alkyl group that may be branched or form a cyclic group, and/or that may be substituted with a halogen atom;

a $C_2$ to $C_8$ alkenyl group that may be branched or form a cyclic group, and/or that may be substituted with a halogen atom;

a $C_2$ to $C_8$ alkynyl group that may be branched or form a cyclic group, and/or that may be substituted with a halogen atom;

an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ (where $R^{30}$ and $R^{31}$ are each independently a hydrogen atom, or a $C_1$ to $C_4$ alkyl group that may be branched and that may be substituted with a halogen atom), or a cyclic amino group that is formed by a $C_2$ to $C_8$ alkylene group; and an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_9$ alkylene group).

In a further embodiment, $R^2$ and $R^{2'}$ of the compound represented by Formula (I) are both hydrogen atoms.

In a further embodiment, $R^2$ and $R^{2'}$ of the compound represented by Formula (I) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

In a further embodiment, $R^4$ and $R^{4'}$ of the compound represented by Formula (I) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

In one embodiment, the inorganic base is used in the form of an aqueous inorganic-base solution.

In a further embodiment, the inorganic base in the aqueous inorganic-base solution is used in a ratio of at least 0.5 equivalents up to 280 equivalents with respect to 1 equivalent of the compound represented by Formula (IV).

In a still further embodiment, a concentration of the aqueous inorganic-base solution is 10 w/w % to 70 w/w %.

In a still further embodiment, the compound represented by Formula (I) is used in a ratio of 0.0001 mol % to 5 mol % with respect to 1 mol of the compound represented by Formula (IV).

In a still further embodiment, a volume ratio between the medium and the aqueous inorganic-base solution is 7:1 to 1:5.

The present invention also provides a method for producing an optically active α-amino acid, the method comprising:

a step of hydrolyzing an imino group ($R^{14}R^{15}C$=$N$—) of a compound represented by Formula (VI) that is obtained using any one of the above-described method under acidic conditions:

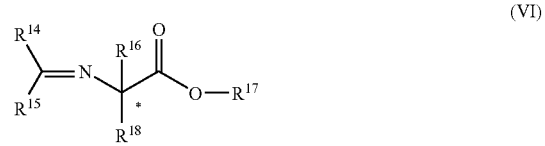

(where $R^{14}$, $R^{15}$, $R^{16}$, $R^{17}$ and $R^{18}$ are the same groups as defined above); and a step of hydrolyzing an ester group (—$CO_2R^{17}$) of the acidic-hydrolysis product under acidic or basic conditions.

The present invention also provides a method for producing an optically active α-amino acid, the method comprising:

a step of hydrolyzing an ester group (—$CO_2R^{17}$) of a compound represented by Formula (VI) that is obtained using any one of the above-described method under basic conditions:

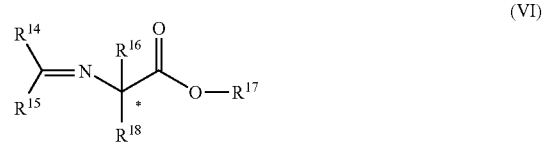

(where $R^{14}$, $R^{15}$, $R^{16}$, $R^{17}$ and $R^{18}$ are the same groups as defined above); and a step of hydrolyzing an imino group ($R^{14}R^{15}C$=$N$—) of the basic-hydrolysis product under acidic conditions.

The present invention provides a chiral phase-transfer catalyst that has a more simplified structure. This phase-transfer catalyst can be produced in a smaller number of process steps than conventional ones. Thus, the phase-transfer catalyst of the present invention, which can be provided more easily, can be used, for example, in the synthesis of α-alkyl-α-amino acid derivatives and α,α-dialkyl-α-amino acids.

BEST MODE FOR CARRYING OUT THE INVENTION

Hereinafter, the terms used in the present invention will be defined.

The phrase "$C_1$ to $C_n$ alkyl group that may be branched or form a cyclic group" (where n is an integer) includes any linear alkyl group having 1 to n carbon atoms, any branched alkyl group having 3 to n carbon atoms, and any cyclic alkyl group having 3 to n carbon atoms. Examples of linear alkyl groups having 1 to 6 carbon atoms include methyl, ethyl, n-propyl, n-butyl, n-pentyl, and n-hexyl. Examples of branched alkyl groups having 3 to 6 carbon atoms include isopropyl, isobutyl, tert-butyl, and isopentyl. Examples of cyclic alkyl groups having 3 to 6 carbon atoms include cyclobutyl, cyclopentyl, and cyclohexyl. Furthermore, when a "$C_1$ to $C_{12}$ alkyl group that may be branched or form a cyclic group and/or that may be substituted with a halogen atom" is referred to, any linear alkyl group having 1 to 12 carbon atoms, any branched alkyl group having 3 to 12 carbon atoms, and any cyclic alkyl group having 3 to 12 carbon atoms are included, and a hydrogen atom at any position of these alkyl groups may be substituted with a halogen atom. Examples of alkyl groups include n-heptyl, isoheptyl, n-octyl, isooctyl, n-decyl, and n-dodecyl.

The phrase "$C_2$ to $C_n$ alkenyl group that may be branched or form a cyclic group" (where n is an integer) includes any linear alkenyl group having 2 to n carbon atoms, any branched alkenyl group having 3 to n carbon atoms, and any cyclic alkenyl group having 3 to n carbon atoms. Examples of linear alkenyl groups having 2 to 6 carbon atoms include ethenyl, 1-propenyl, 2-propenyl, 1-butenyl, 2-butenyl, 1-pentenyl, 2-pentenyl, 3-pentenyl, 4-pentenyl, and 1-hexenyl. Examples of branched alkenyl groups having 3 to 6 carbon atoms include isopropenyl, 1-methyl-1-propenyl, 1-methyl-2-propenyl, 2-methyl-1-propenyl, 2-methyl-2-propenyl, and 1-methyl-2-butenyl. Examples of cyclic alkenyl groups having 3 to 6 carbon atoms include cyclobutenyl, cyclopentenyl, and cyclohexenyl. Furthermore, when a "$C_2$ to $C_{12}$ alkenyl group that may be branched or form a cyclic group, and/or that may be substituted with a halogen atom" is referred to, any linear alkenyl group having 2 to 12 carbon atoms, any branched alkenyl group having 3 to 12 carbon atoms, and any cyclic alkenyl group having 3 to 12 carbon atoms are included, and a hydrogen atom at any position of these alkenyl groups may be substituted with a halogen atom. Examples of such alkenyl groups include 1-heptenyl, 2-heptenyl, 1-octenyl, 1-decenyl, and 1-dodecenyl.

The phrase "$C_2$ to $C_n$ alkynyl group that may be branched or form a cyclic group" (where n is an integer) includes any linear alkynyl group having 2 to n carbon atoms, any branched alkynyl group having 3 to n carbon atoms, and any cyclic alkynyl group having 3 to n carbon atoms. Examples of linear alkynyl groups having 2 to 6 carbon atoms include ethynyl, 1-propynyl, 1-butynyl, 2-butynyl, 1-pentynyl, and 1-hexynyl. Examples of branched alkynyl groups having 3 to 6 carbon atoms include 1-methyl-2-propynyl. Examples of cyclic alkynyl groups having 3 to 6 carbon atoms include cyclopropylethynyl and cyclobutylethynyl. Furthermore, when a "$C_2$ to $C_{12}$ alkynyl group that may be branched or form a cyclic group, and/or that may be substituted with a halogen atom" is referred to, any linear alkynyl group having 1 to 12 carbon atoms, any branched alkynyl group having 3 to 12 carbon atoms, and any cyclic alkynyl group having 3 to 12 carbon atoms are included, and a hydrogen atom at any position of these alkynyl groups may be substituted with a halogen atom. Examples of such alkynyl groups include 1-heptynyl, 1-octynyl, 1-decynyl, and 1-dodecynyl.

The phrase "$C_1$ to $C_n$ alkoxy group that may be branched" (where n is an integer) includes alkoxy groups having any linear alkyl groups having 1 to n carbon atoms and alkoxy groups having any branched alkyl groups having 3 to n carbon atoms. Examples thereof include methyloxy, ethyloxy, n-propyloxy, isopropyloxy, and tert-butyloxy.

In the present invention, examples of an "aralkyl group" include benzyl, phenethyl, naphthylmethyl, 3-phenylpropyl, 2-phenylpropyl, 4-phenylbutyl, and 2-phenylbutyl.

In the present invention, examples of an "aryl group" include phenyl, naphthyl, anthryl, and phenanthryl.

In the present invention, examples of a "halogen atom" include a chlorine atom, a bromine atom, an iodine atom, and a fluorine atom. In the present invention, the term "halide anion" refers to halogen ions and examples thereof include a chloride ion, a bromide ion, an iodide ion, and a fluoride ion.

In the present invention, the phrase "$C_3$ to $C_n$ propargyl group or substituted propargyl group that may be branched" (where n is an integer) refers to a propargyl group or any substituted propargyl group having a substituent(s) at position 1 and/or 3 and having 4 to n carbon atoms in total. Examples thereof include 2-propynyl and 3-trimethylsilyl-2-propynyl.

Hereinafter, the present invention will be described more specifically.

<Quaternary Ammonium Salt>

The compound of the present invention is a novel quaternary ammonium salt, and is preferably pure with respect to its axial asymmetry in the production of an optically active α-amino acid derivative and the like described later. The compound of the present invention can be represented by Formula (I) below:

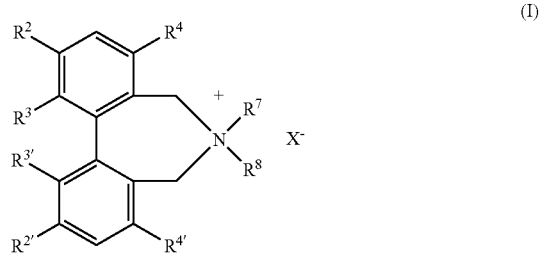

(where $R^2$ and $R^{2'}$ are each independently:

a hydrogen atom; or an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom;

$R^3$ and $R^{3'}$ are each independently:

a $C_1$ to $C_5$ alkoxy group that may be substituted with a halogen atom and/or an aryl group, and/or that may be branched or form a cyclic group;

$R^4$ and $R^{4'}$ are each independently a group selected from the group consisting of:

(i) a hydrogen atom;

(ii) a halogen atom;

(iii) a $C_1$ to $C_6$ alkyl group that may be branched or form a cyclic group and that may be substituted with a halogen atom;

(iv) a $C_2$ to $C_6$ alkenyl group that may be branched or form a cyclic group and that may be substituted with a halogen atom;

(v) a $C_2$ to $C_6$ alkynyl group that may be branched or form a cyclic group and that may be substituted with a halogen atom;

(vi) an aralkyl group, wherein the aryl moiety constituting the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; and (vii) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom;

$R^7$ and $R^8$ are each independently a monovalent organic group or taken together to form a divalent organic group, and $X^-$ is an anion selected from the group consisting of a halide anion, $SCN^-$, $HSO_4^-$, $HF_2^-$, $CF_3SO_3^-$, $CH_3-C_6H_4-SO_3^-$, and $CH_3SO_3^-$).

The compound represented by Formula (I) functions usefully as a phase-transfer catalyst for producing, for example, an optically active α-amino acid or a derivative thereof, and, in particular, an α,α-dialkyl-α-amino acid or a derivative thereof as described later. More specifically, if the compound represented by Formula (I) is used as a phase-transfer catalyst in order to produce an optically active α-amino acid or a derivative thereof represented by Formula (VI) by alkylating the compound represented by Formula (IV) with the compound represented by Formula (V), the ammonium moiety constituting a cation of this compound:

contributes to the reactivity in the alkylation, and the biphenyl moiety that is pure with respect to its axial asymmetry:

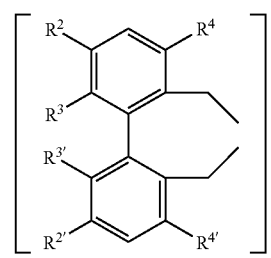

contributes to the stereoselectivity of the alkylation reaction. Therefore, in one embodiment, $R^7$ and $R^8$ of the compound represented by Formula (I) are groups that can retain the catalytic activity and stereoselectivity arising from the ammonium moiety and the biphenyl moiety of the cation, respectively (or inhibit neither catalytic activity nor selectivity). For example, they can be monovalent organic groups or divalent organic groups that are inactive compared to the ammonium moiety and the biphenyl moiety. In other words, it is not necessary for $R^7$ and $R^8$ to be groups which themselves (or itself) have excellent reactivity, and they may be any substituent, as long as they do not adversely affect the reactions involved in the production of the amino acid or derivative thereof as described later. Alternatively, if the compound represented by Formula (I) is used as a phase-transfer catalyst for producing an optically active α-amino acid or a derivative thereof as described later, $R^7$ and $R^8$ in Formula (I) are each independently a group selected from the group consisting of:

(i) a $C_1$ to $C_{30}$ alkyl group that may be branched or form a cyclic group and that may be substituted with a halogen atom;

(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom; and (iv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom; or $R^7$ and $R^8$ are taken together to form a (divalent organic) group selected from the group consisting of:

—$(CH_2)_m$— (where m is an integer from 2 to 8);

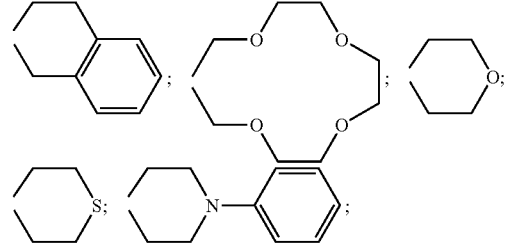

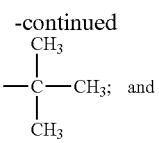

-continued

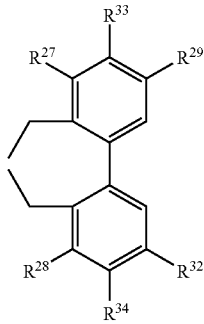

(where $R^{27}$, $R^{28}$, $R^{29}$, $R^{32}$, $R^{33}$ and $R^{34}$ are each independently a group selected from the group consisting of:

a hydrogen atom;

a $C_1$ to $C_8$ alkyl group that may be branched or form a cyclic group, and/or that may be substituted with a halogen atom;

a $C_2$ to $C_8$ alkenyl group that may be branched or form a cyclic group, and/or that may be substituted with a halogen atom;

a $C_2$ to $C_8$ alkynyl group that may be branched or form a cyclic group, and/or that may be substituted with a halogen atom;

an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group; and an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group).

In the present invention, it is preferable that $R^2$ and $R^{2'}$ of the compound represented by Formula (I) are both hydrogen atoms.

Alternatively, in the present invention, it is preferable that $R^2$ and $R^{2'}$ of the compound represented by Formula (I) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

Alternatively, in the present invention, it is preferable that $R^7$ and $R^8$ of the compound represented by Formula (I) are each independently a $C_1$ to $C_{30}$ alkyl group that may be branched or form a cyclic group and that may be substituted with a halogen atom. Alternatively, in this specification, it is preferable that $R^7$ and $R^8$ are each independently a $C_1$ to $C_{12}$ alkyl group that may be branched or form a cyclic group and that may be substituted with a halogen atom, or a $C_{13}$ to $C_{30}$ alkyl group that may be branched or form a cyclic group and that may be substituted with a halogen atom (more preferably, a $C_{13}$ to $C_{22}$ alkyl group that may be branched or form a cyclic group and that may be substituted with a halogen atom). Alternatively, in this specification, it is preferable that $R^7$ and $R^8$ are each independently an alkyl group that may be branched or form a cyclic group and that may be substituted with a halogen atom, and it is more preferable that the number of carbon atoms constituting the alkyl group can be selected from a range in which the lower limit is at least 1, at least 3, at least 13, at least 15, at least 17, or at least 18, and the upper limit is not more than 30, not more than 22, not more than 21, not more than 20, not more than 12, not more than 8, or not more than 4. In particular, in Formula (I), it is preferable that $R^7$ and $R^8$ of the compound are both n-butyl groups. The reason for this is that if a compound represented by Formula (I) having such a substituent group is used as a catalyst (e.g., phase-transfer catalyst) to produce an optically active α-amino acid and a derivative thereof, and preferably an α,α-dialkyl-α-amino acid or a derivative thereof, then the amino acid or a derivative thereof can be produced with excellent yield and optical purity.

Alternatively, in the present invention, it is preferable that $R^2$ and $R^{2'}$ of the compound represented by Formula (I) are the same.

Alternatively, in the present invention, it is preferable that $R^3$ and $R^{3'}$ of the compound represented by Formula (I) are the same.

Alternatively, in the present invention, it is preferable that $R^4$ and $R^{4'}$ of the compound represented by Formula (I) are the same.

Alternatively, in the present invention, it is preferable that $R^7$ and $R^8$ of the compound represented by Formula (I) are the same.

<Method of Producing the Quaternary Ammonium Salt>

The quaternary ammonium salt represented by Formula (I) can be produced by reacting a compound represented by Formula (II) below:

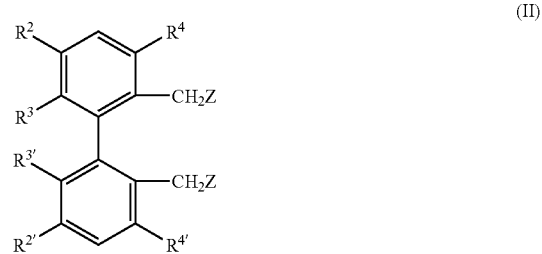

with a secondary amine represented by Formula (III) below:

$$HN\begin{matrix}R^7\\R^8\end{matrix} \quad (III)$$

in an organic solvent in the presence of an acid-scavenging agent.

Here, in Formula (II), $R^2$ and $R^{2'}$ are each independently:
  a hydrogen atom; or
  an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom or a $C_1$ to $C_4$ alkyl group that may be branched and that may be substituted with a halogen atom, and
    a halogen atom;

$R^3$ and $R^{3'}$ are each independently:
  a $C_1$ to $C_5$ alkoxy group that may be substituted with a halogen atom and/or an aryl group, and/or that may be branched or form a cyclic group;

$R^4$ and $R^{4'}$ are each independently a group selected from the group consisting of:
  (i) a hydrogen atom;
  (ii) a halogen atom;
  (iii) a $C_1$ to $C_6$ alkyl group that may be branched or form a cyclic group and that may be substituted with a halogen atom;
  (iv) a $C_2$ to $C_6$ alkenyl group that may be branched or form a cyclic group and that may be substituted with a halogen atom;
  (v) a $C_2$ to $C_6$ alkynyl group that may be branched or form a cyclic group and that may be substituted with a halogen atom;
  (vi) an aralkyl group, wherein the aryl moiety constituting the aralkyl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom or a $C_1$ to $C_4$ alkyl group that may be branched and that may be substituted with a halogen atom, and
    a halogen atom; and
  (vii) an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom or a $C_1$ to $C_4$ alkyl group that may be branched and that may be substituted with a halogen atom, and
    a halogen atom, and Z is a halogen atom, and in Formula (III), $R^7$ and $R^8$ are each independently a group selected from the group consisting of:
  (i) a $C_1$ to $C_{30}$ alkyl group that may be branched or form a cyclic group and that may be substituted with a halogen atom;
  (ii) a $C_2$ to $C_{12}$ alkenyl group that may be branched or form a cyclic group and that may be substituted with a halogen atom;
  (iii) a $C_2$ to $C_{12}$ alkynyl group that may be branched or form a cyclic group and that may be substituted with a halogen atom; and
  (iv) an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom or a $C_1$ to $C_4$ alkyl group that may be branched and that may be substituted with a halogen atom, and
    a halogen atom; or $R^7$ and $R^8$ are taken together to form a (divalent) group selected from the group consisting of:
  —$(CH_2)_m$— (where m is an integer from 2 to 8);

[structures shown: tetralin-like bicyclic; crown ether (1,4,7,10-tetraoxacyclododecane-type); tetrahydropyran (O); thiane (S); N-phenylpiperazine; piperidine-N—C(=O)—O—C(CH$_3$)$_3$ (Boc-piperidine); and a biphenyl bearing substituents $R^{27}$, $R^{28}$, $R^{29}$, $R^{32}$, $R^{33}$, $R^{34}$]

(where $R^{27}$, $R^{28}$, $R^{29}$, $R^{32}$, $R^{33}$ and $R^{34}$ are each independently a group selected from the group consisting of:
  a hydrogen atom;
  a $C_1$ to $C_8$ alkyl group that may be branched or form a cyclic group, and/or that may be substituted with a halogen atom;
  a $C_2$ to $C_8$ alkenyl group that may be branched or form a cyclic group, and/or that may be substituted with a halogen atom;

a $C_2$ to $C_8$ alkynyl group that may be branched or form a cyclic group, and/or that may be substituted with a halogen atom;

an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, $-NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group; and an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, $-NR^{30}R^{31}$ (where $R^{30}$ and $R^{31}$ are each independently a hydrogen atom or a $C_1$ to $C_4$ alkyl group that may be branched and that may be substituted with a halogen atom), or a cyclic amino group that is formed by a $C_2$ to $C_8$ alkylene group).

In the present invention, it is preferable that $R^2$ and $R^{2'}$ of the compound represented by Formula (II) are both hydrogen atoms.

Alternatively, in the present invention, it is preferable that $R^2$ and $R^{2'}$ of the compound represented by Formula (II) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

Alternatively, in the present invention, it is preferable that $R^4$ and $R^{4'}$ of the compound represented by Formula (II) are both aryl groups, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom or a $C_1$ to $C_4$ alkyl group that may be branched and that may be substituted with a halogen atom, and a halogen atom.

Alternatively, in the present invention, it is preferable that $R^2$ and $R^{2'}$ of the compound represented by Formula (II) are the same.

Alternatively, in the present invention, it is preferable that $R^3$ and $R^{3'}$ of the compound represented by Formula (II) are the same.

Alternatively, in the present invention, it is preferable that $R^4$ and $R^{4'}$ of the compound represented by Formula (II) are the same.

Alternatively, in the present invention, it is preferable that $R^7$ and $R^8$ of the compound represented by Formula (II) are the same.

The compound of Formula (II) used in the present invention can be synthesized, for example, using the following method.

First, a compound (6,6'-dimethylbiphenyl-2,2'-diol) represented by the following formula:

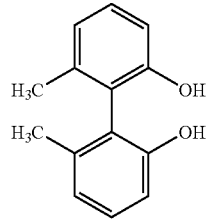

is prepared as a starting material. Either the S-form or the R-form of the 6,6'-dimethylbiphenyl-2,2'-diol can be used according to the absolute configuration of the compound (I) of the present invention that is to be finally produced. The 6,6'-dimethylbiphenyl-2,2'-diol itself has a known structure, and can be synthesized, for example, according to the following reaction scheme. A synthetic method according to the reaction scheme is known, for example, in Japanese Laid-Open Patent Publication No. 2004-189696.

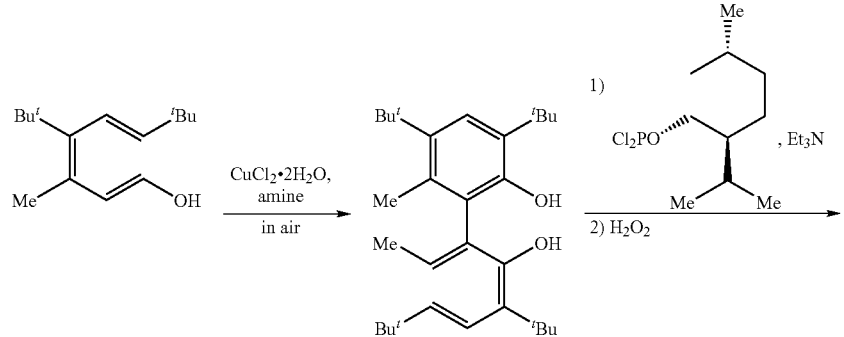

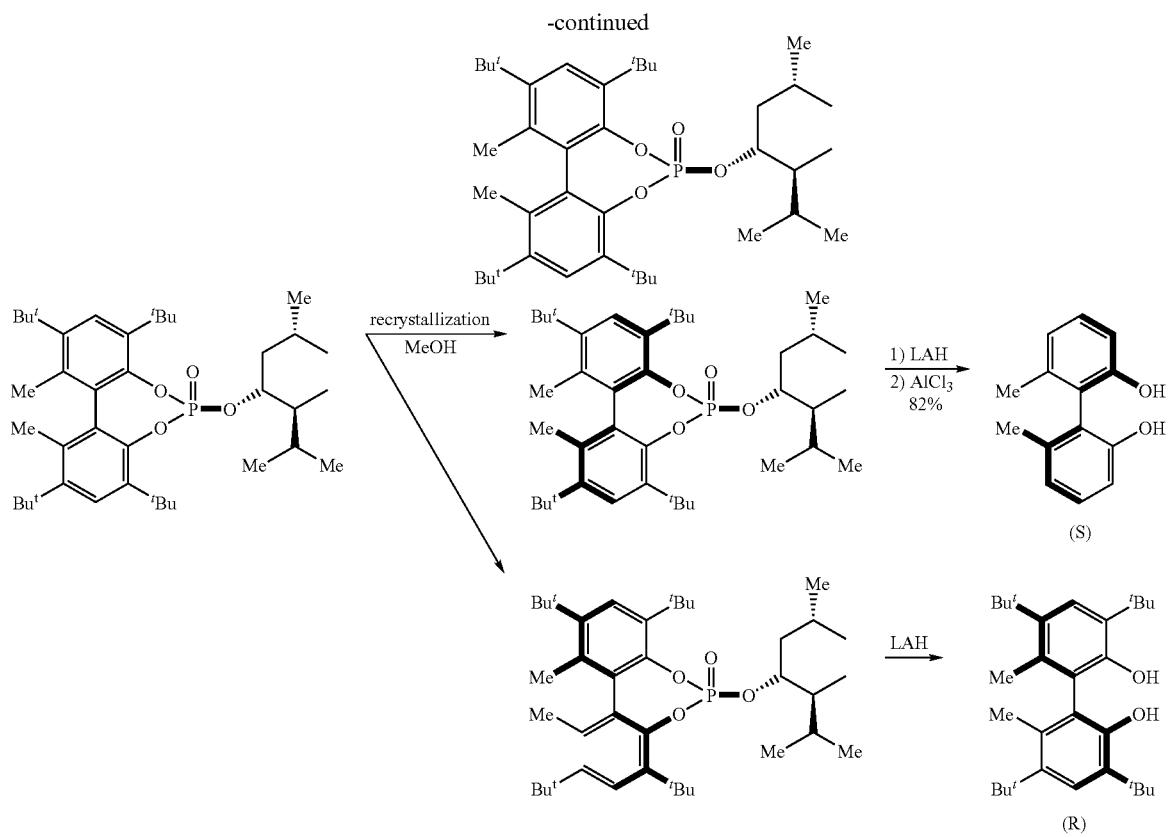

This 6,6'-dimethylbiphenyl-2,2'-diol is reacted with an alkylating agent in an organic solvent such as acetone in the presence of an acid-scavenging agent (e.g., inorganic bases such as potassium carbonate, sodium carbonate, potassium hydrogen carbonate, and sodium hydrogen carbonate).

Examples of the alkylating agent include a compound represented by $R^{40}Y$ (where $R^{40}$ is a $C_1$ to $C_5$ alkyl group that may be substituted with a halogen atom and/or an aryl group, and/or that may be branched or form a cyclic group, and Y is a halogen atom or a group represented by the following formula:

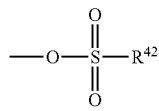

(where $R^{42}$ is a $C_1$ to $C_5$ alkyl group that may be substituted with a halogen atom, an alkyl group, or a nitro group, or an aryl group that may be substituted with a halogen atom, an alkyl group, or a nitro group)). Preferable examples of the alkylating agent include methyl iodide and isopropyl iodide. The thus obtained 6,6'-dimethyl-2,2'-dialkoxy biphenyl is reacted with a halogenating agent such as bromine ($Br_2$) in an organic solvent such as dichloromethane.

The compound thus obtained can be obtained also by halogenating, before the reaction with the alkylating agent, the 6,6'-dimethylbiphenyl-2,2'-diol at positions 3,3',5 and 5' using bromine ($Br_2$) or the like, and then reacting the resultant with an alkylating agent in an organic solvent such as acetone in the presence of an acid-scavenging agent (e.g., inorganic bases such as potassium carbonate, sodium carbonate, potassium hydrogen carbonate, and sodium hydrogen carbonate).

In this manner, it is possible to obtain a compound represented by Formula (VII) below:

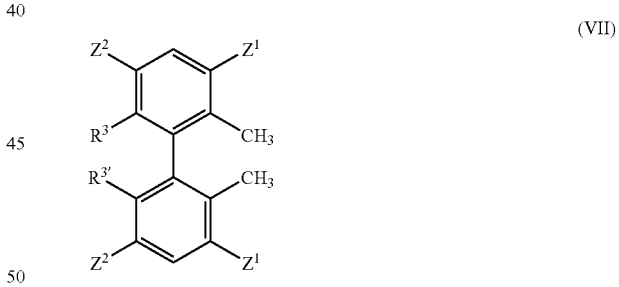

(where
$R^3$ and $R^{3'}$ are each independently:
a $C_1$ to $C_5$ alkoxy group that may be substituted with a halogen atom and/or an aryl group, and/or that may be branched or form a cyclic group,
$Z^1$ is a halogen atom, and
$Z^2$ is a hydrogen atom or a halogen atom).

The compound of Formula (VII) is then subjected to the Suzuki-Miyaura coupling reaction with at least one type of boronic acid derivative represented by $R^4$—$B(OH)_2$ or $R^{4'}$—$B(OH)_2$ (where $R^4$ and $R^{4'}$ are each independently the same groups as defined above) in an organic solvent such as N,N-dimethylformamide (DMF) in the presence of a palladium catalyst. Specific examples of the boronic acid derivative include 3,4,5-trifluorophenylboronic acid. Subsequently, the methyl group of this compound is halogenated by means used ordinarily in the art, so that it is possible to obtain the compound represented by Formula (II).

On the other hand, in the method for producing the compound represented by Formula (I) of the present invention, a large number of the secondary amines of Formula (III) are commercially available and can be easily obtained, or they can be easily produced using known methods.

Examples of the organic solvents used in the reaction process for producing the compound of Formula (I) of the present invention include nitrile solvents (e.g., acetonitrile, propionitrile), ether solvents (e.g., dioxane, tetrahydrofuran, isopropyl ether, diethyl ether, dimethoxyethane, 2-methoxyethyl ether), alcohol solvents (e.g., methanol, ethanol, n-propanol, isopropanol, n-butanol, tert-butanol), ester solvents (e.g., ethyl acetate, isopropyl acetate), and amide solvents (e.g., DMF, N,N-dimethylacetamide). In the present invention, acetonitrile is particularly preferable. Examples of the acid-scavenging agents include inorganic bases, such as potassium carbonate, sodium carbonate, potassium hydrogen carbonate, and sodium hydrogen carbonate.

In the reaction, the secondary amine of Formula (III) is used preferably in 0.5 to 10 equivalents, and more preferably in 0.8 to 3 equivalents, with respect to the compound of Formula (II). The acid-scavenging agent is preferably used in 0.5 to 10 equivalents, and more preferably in 0.8 to 5 equivalents, with respect to the compound of Formula (II). The reaction between the compound of Formula (II) and the secondary amine of Formula (III) is carried out in a suitable organic solvent in the presence of the acid-scavenging agent preferably with stirring. The reaction temperature is preferably from room temperature to the boiling point of the organic solvent used, and more preferably the reaction is performed while heating under reflux. The reaction time is preferably 15 minutes to 24 hours, and more preferably 30 minutes to 12 hours. In this case, the organic solvent is used in an amount, for example, 5 to 50 times or 6 to 30 times the amount of the compound of Formula (II) at a volume (ml)/weight (g) ratio. After the reaction is complete, the reaction mixture is extracted with dichloromethane, dichloroethane, chloroform, or ethyl acetate, and isolation and purification by silica gel column chromatography are performed to obtain the compound of Formula (I). Alternatively, the reaction mixture may be used without further treatment as a phase-transfer catalyst in the method for producing α-amino acid derivatives specifically described later.

The thus obtained compound of Formula (I) in which X⁻ is a halide anion is in a pure form with respect to axial asymmetry, and can be used as a phase-transfer catalyst. Here, "pure with respect to axial asymmetry" means that, in various stereoisomers formed based on the axial asymmetry, one specific isomer is more abundant than the other. The abundance ratio of the one specific isomer is preferably 90% or more, more preferably 95% or more, and even more preferably 98% or more.

Furthermore, the compound of Formula (I) in which X⁻ is a halide anion can be converted to a compound in which the halide anion is replaced by SCN⁻, $HSO_4^-$, $HF_2^-$, $CF_3SO_3^-$, $CH_3$—$C_6H_4$—$SO_3^-$ (may be referred to as $CH_3$-Ph-$SO_3^-$), or $CH_3SO_3^-$, for example, according to the following processes.

First, a method for producing the compound of Formula (I) in which X⁻ is SCN⁻ or $HSO_4^-$ will be described.

The thus obtained compound of Formula (I) in which X⁻ is a halide anion is dissolved in, for example, a suitable second organic solvent according to the method described in Japanese Laid-Open Patent Publication No. 2002-173492 and the solution is mixed with a saturated aqueous solution of an alkali metal salt of thiocyanic acid so that the halide anion of X⁻ is converted to SCN⁻.

Examples of the second organic solvent that can be used in this conversion include dichloromethane, chloroform, dichloroethane, tetrahydrofuran, methyl t-butyl ether, diisopropyl ether, and ethyl acetate. Examples of alkali metal salts of thiocyanic acid include potassium thiocyanate and sodium thiocyanate.

For example, by bringing the compound of Formula (I) in which X⁻ is a halide anion into contact with an alkali metal salt of thiocyanic acid in a solution under relatively mild conditions such as at room temperature through mixing, the reaction can proceed easily, and the reaction product (that is, the compound of Formula (I) in which X⁻ is SCN⁻) can be obtained in a quantitative yield.

Furthermore, by reacting the compound of Formula (I) in which X⁻ is SCN⁻ with a concentrated sulfuric acid solution, X⁻ can be easily converted from SCN⁻ to $HSO_4^-$.

The thus obtained compound of Formula (I) in which X⁻ is $HSO_4^-$ can then be further reacted with an alkali metal fluoride (e.g., potassium fluoride, sodium fluoride or lithium fluoride) to obtain a compound represented by Formula (Ia):

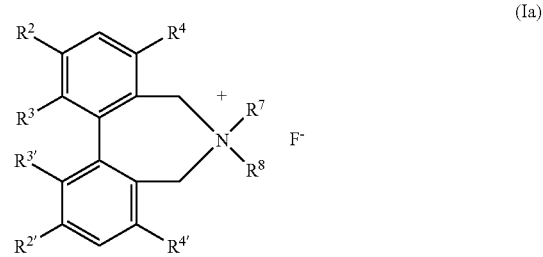

(Ia)

(where $R^2$, $R^{2'}$, $R^3$, $R^{3'}$, $R^4$, $R^{4'}$, $R^7$ and $R^8$ are each independently the same as those defined in Formula (I)), which can be used as a catalyst, for example, in a reaction of a silyl enol ether with a carbonyl compound (aldol reaction).

Examples of the silyl enol ethers used in the aldol reaction include a trialkylsilyl enol ether. A trialkylsilyl enol ether can be prepared in advance by reacting a chlorosilane, such as trimethylsilyl chloride and triethylsilyl chloride, with carbonyl compounds (e.g., ketonic carbonyl derivatives, such as 2-butanone, 4-penten-2-one, diethyl ketone, acetophenone, propiophenone, butyronaphtone, cyclohexanone, 1-oxoindan, 1-tetralone or 2-tetralone) in the presence of a base.

In addition to the above-mentioned carbonyl compounds (the above-described ketonic carbonyl derivatives), which function as precursors of the silyl enol ethers, examples of the carbonyl compounds that can be used to prepare silyl enol ethers for the aldol reaction include aldehyde compounds, such as acetylaldehyde, propionaldehyde, butylaldehyde, isobutylaldehyde, isovaleraldehyde, capronaldehyde, dodecylaldehyde, palmitinaldehyde, stearinaldehyde, acrolein, crotonaldehyde, cyclohexanecarbaldehyde, benzaldehyde, anisaldehyde, nicotinaldehyde, cinnamaldehyde, (x-naphthaldehyde, and β-naphthaldehyde.

With respect to such a silyl enol ether and such a carbonyl compound, the compound represented by Formula (Ia) is used as a catalyst in the aldol reaction to control the stereoselectivity of the reaction.

Next, a method for producing the compound of Formula (I) in which X⁻ is $HF_2^-$, $CF_3SO_3^-$, $CH_3$-Ph-$SO_3^-$, or $CH_3SO_3^-$ will be described.

The compound of Formula (I) obtained in the above-described manner in which X⁻ is a halide anion is brought in contact with an ion-exchange resin to produce a first intermediate.

The ion-exchange resin can be freely selected by those skilled in the art. Specific examples of the ion-exchange resin that can be used include Amberlyst A26 (OH) (manufactured by ORGANO CORPORATION).

The compound of Formula (I) in which X⁻ is a halide anion and the ion-exchange resin can be brought in contact by dissolving the compound of Formula (I) in which X⁻ is a halide anion in a suitable third solvent and passing this solution through a column filled with the ion-exchange resin. An alcohol solvent is preferable as the third solvent that can be used for such a contact. Specific examples of alcohol solvents include methyl alcohol, ethyl alcohol, isopropyl alcohol, and normal propyl alcohol, but are not limited thereto.

There is no specific limitation on the amount of the compound of Formula (I) in which X⁻ is a halide anion and the amount of the third solvent used for such contact, and they can be appropriately set by those skilled in the art.

Thus, the first intermediate is produced.

Next, the first intermediate thus obtained is treated with an acid solution (e.g., a hydrogen fluoride aqueous solution, a methanesulfonic acid solution, a toluenesulfonic acid solution, or a trifluoromethanesulfonic acid solution) preferably without removing the solvent described above.

There is no specific limitation on the amount of hydrogen fluoride aqueous solution or sulfonic acid solution used in the present invention. In view of increasing the productivity, it is preferable that the amount is chosen so that an equal or greater amount of hydrogen fluoride or sulfonic acid is reacted with the compound of Formula (I) used above in which X⁻ is a halide anion. Thus, a compound represented by any of Formulae (Ib) to (Ie):

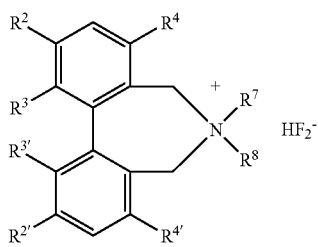
(Ib)

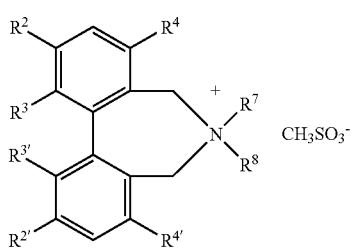
(Ic)

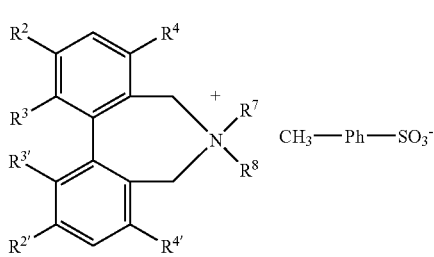
(Id)

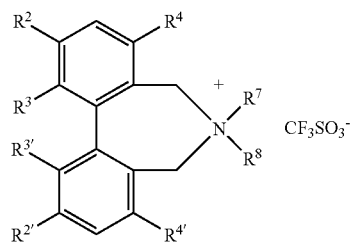
(Ie)

in which the quaternary ammonium moiety is liberated from the first intermediate, and X— is further converted from a halide anion to $HF_2^-$, $CF_3SO_3^-$, $CH_3\text{-}Ph\text{-}SO_3^-$, or $CH_3SO_3^-$ can be precipitated from the solution.

The compounds of Formulae (Ib) to (Ie) can be easily isolated by removing the solvent using means employed ordinarily by those skilled in the art.

The thus obtained compounds of Formulae (Ib) to (Ie), and particularly the compound of Formula (Ib), can also be utilized as a catalyst for producing a nitroalcohol diastereo- and enantioselectively.

<Method for Producing α-Amino Acid Derivatives>

Next, a method for producing α-amino acid derivatives using the quaternary ammonium compound of the present invention represented by Formula (I) as a phase-transfer catalyst will be described.

An α-amino acid derivative represented by Formula (VI):

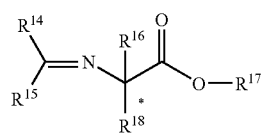
(VI)

(where
$R^{14}$ and $R^{15}$ are each independently:
(i) a hydrogen atom; or
(ii) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom or a $C_1$ to $C_4$ alkyl group that may be branched and that may be substituted with a halogen atom, and
a halogen atom,
with the proviso that the case where $R^{14}$ and $R^{15}$ are both hydrogen atoms is excluded;
$R^{16}$ is a group selected from the group consisting of:
(i) a hydrogen atom;
(ii) a $C_1$ to $C_{10}$ alkyl group that may be branched or form a cyclic group and that may be substituted with a halogen atom, wherein the alkyl group may be substituted with a $C_1$ to $C_5$ alkoxy group that may be branched and that may be substituted with a halogen atom;
(iii) a $C_2$ to $C_6$ alkenyl group that may be branched or form a cyclic group and that may be substituted with a halogen atom;
(iv) a $C_2$ to $C_6$ alkynyl group that may be branched or form a cyclic group and that may be substituted with a halogen atom;

(v) an aralkyl group, wherein the aryl moiety constituting the aralkyl group may be substituted with at least one group selected from the group consisting of:
   a $C_1$ to $C_4$ alkyl group that may be branched and that may be substituted with a halogen atom,
   a $C_1$ to $C_5$ alkoxy group that may be branched and that may be substituted with a halogen atom,
   an aryl group that may be substituted with a halogen atom or a $C_1$ to $C_4$ alkyl group that may be branched and that may be substituted with a halogen atom, and
   a halogen atom; and
(vi) an aryl group, wherein the aryl group may be substituted with at least one group selected from the group consisting of:
   a $C_1$ to $C_4$ alkyl group that may be branched and that may be substituted with a halogen atom,
   a $C_1$ to $C_5$ alkoxy group that may be branched and that may be substituted with a halogen atom,
   an aryl group that may be substituted with a halogen atom or a $C_1$ to $C_4$ alkyl group that may be branched and that may be substituted with a halogen atom, and
   a halogen atom;
$R^{17}$ is a $C_1$ to $C_8$ alkyl group that may be branched or form a cyclic group;
$R^{18}$ is a group selected from the group consisting of:
   (i) a $C_1$ to $C_{10}$ alkyl group that may be branched or form a cyclic group and that may be substituted with a halogen atom, wherein the alkyl group may be substituted with a $C_1$ to $C_5$ alkoxy group that may be branched and that may be substituted with a halogen atom;
   (ii) a $C_2$ to $C_6$ alkenyl group that may be branched or form a cyclic group and that may be substituted with a halogen atom;
   (iii) a $C_2$ to $C_6$ alkynyl group that may be branched or form a cyclic group and that may be substituted with a halogen atom;
   (iv) an aralkyl group, wherein the aryl moiety constituting the aralkyl group may be substituted with at least one group selected from the group consisting of:
      a $C_1$ to $C_4$ alkyl group that may be branched and that may be substituted with a halogen atom,
      a $C_1$ to $C_5$ alkoxy group that may be branched and that may be substituted with a halogen atom,
      an aryl group that may be substituted with a halogen atom or a $C_1$ to $C_4$ alkyl group that may be branched and that may be substituted with a halogen atom, and
      a halogen atom; and
   (v) a $C_3$ to $C_9$ propargyl group or substituted propargyl group that may be branched and that may be substituted with a halogen atom; and * indicates a newly produced asymmetric center) can be produced stereoselectively through the process of alkylating the compound represented by Formula (IV):

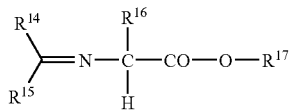

(IV)

(where $R^{14}$, $R^{15}$, $R^{16}$ and $R^{17}$ are the same as those defined in Formula (VI))
with a compound of Formula (V):

$R^{18}—W$   (V)

(where $R^{18}$ is the same as that defined in Formula (VI), and W is a functional group having a leaving ability)
using the compound represented by Formula (I) as a phase-transfer catalyst in a medium in the presence of an inorganic base.

Examples of the medium used in the alkylation process include benzene, toluene, xylene, ethyl ether, isopropyl ether, tetrahydrofuran, dioxane, ethyl acetate, isopropyl acetate, cyclopentyl methyl ether, and methyl t-butyl ether. Alternatively, the medium may also be a biphasic one containing water and a medium immiscible with water. The medium can be used preferably 0.5 to 30 times, and more preferably 1 to 25 times the amounts of the compound of Formula (IV) at a ratio of volume (ml)/weight (g).

Examples of the inorganic base used in the alkylation process include lithium hydroxide, sodium hydroxide, potassium hydroxide, calcium hydroxide, rubidium hydroxide, and cesium hydroxide. The inorganic base can be used preferably in 0.5 to 100 equivalents, and more preferably in 0.8 to 40 equivalents, with respect to the compound of Formula (IV).

In the alkylation process, an inorganic base may be used in the form of an aqueous inorganic-base solution. In the case where an inorganic base is used in the form of an aqueous inorganic-base solution, the upper limit of the inorganic base that can be contained in the aqueous inorganic-base solution is preferably 280 equivalents or less, more preferably 150 equivalents or less, and even more preferably 56 equivalents or less, with respect to the compound of Formula (IV). The lower limit of the inorganic base that can be contained in the aqueous inorganic-base solution is preferably 0.5 equivalents or more, more preferably 0.8 equivalents or more, and even more preferably 0.9 equivalents or more, with respect to the compound of Formula (IV). The aqueous inorganic-base solution may be used preferably in 5 w/w % to 70 w/w %, and more preferably in 10 w/w % to 60 w/w %.

The volume ratio between the medium and the aqueous inorganic-base solution is preferably a medium volume (ml)/aqueous inorganic-base solution (ml) ratio of 7/1 to 1/5, more preferably 5/1 to 1/3, and even more preferably 4/1 to 1/1.

In the alkylation process, the compound of Formula (V) is used preferably in 0.5 to 10 equivalents, more preferably in 0.7 to 6 equivalents, and even more preferably in 0.9 to 5 equivalents, with respect to the compound of Formula (IV). The compound of Formula (I) is used as a phase-transfer catalyst preferably in amounts at a lower limit of not less than 0.0001 mol % and more preferably not less than 0.0005 mol %, and at an upper limit of preferably not more than 10 mol %, more preferably not more than 2 mol %, even more preferably not more than 1 mol %, and yet even more preferably not more than 0.5 mol %, with respect to 1 mol of the compound of Formula (IV). Thus, the phase-transfer catalyst used in the present invention has extremely high activity, and therefore by using the catalyst only in a very small amount with respect to 1 mol of the compound of Formula (IV), the desired optically active α-amino acids and derivatives thereof can be obtained.

Furthermore, in the present invention, in addition to the asymmetrical phase-transfer catalyst represented by Formula (I), an achiral quaternary ammonium salt, such as tetrabutylammonium bromide (TBAB), can also be used together. For example, TBAB functions as a cocatalyst in the reaction system of the present invention to improve the yield of α-amino acids and derivatives thereof, and also allows the amount of the asymmetrical phase-transfer catalyst represented by Formula (I) that is used in the present invention to be further reduced. The amount of TBAB that can be used in the present invention is preferably 0.005 mol % to 1 mol %, and more preferably 0.01 mol % to 0.8 mol %, with respect to 1 mol of the compound of Formula (IV).

The alkylation process is performed at suitable temperatures between −70° C. and room temperature, preferably between −20° C. and 20° C., in air, under a nitrogen atmosphere, or under an argon atmosphere. This process can be performed with stirring for a suitable period until the alkylation reaction has sufficiently proceeded. The reaction time is preferably 30 minutes to 48 hours, and more preferably 1 hour to 24 hours.

When the aqueous inorganic-base solution is used in the alkylation process, it is preferable to split the process into multiple operations, as described below.

In other words, at first, the compound of Formula (IV), the phase-transfer catalyst of Formula (I), and the compound of Formula (V) are each added to the medium to prepare a mixture. At this time, it is preferable to sufficiently stir the mixture with cooling using, for example, ice or ice-salt. To the cooled mixture is then added the aqueous inorganic-base solution to alkylate the compound of Formula (IV). The temperatures set to cool the mixture are preferably between −20° C. and 20° C., more preferably between −15° C. and 15° C., and even more preferably between −10° C. and 10° C.

According to the method of the present invention using the compound of Formula (I) as described above, the optically active compound of Formula (VI) can be obtained in a high yield and high optical purity. Here, high optical purity refers to an optical purity of preferably at least 80% ee, more preferably at least 85% ee, yet more preferably at least 90% ee, and even more preferably at least 95% ee.

<Method for Producing α-Amino Acid>

In another aspect of the present invention, a method for producing optically active α-amino acids is provided.

In the present invention, an optically active α-amino acid can be produced by performing, for example, either one of the following procedures, using the optically active compounds of Formula (VI) (optically active α-amino acid derivatives) obtained by the method described above.

In the first method, first, the imino group ($R^{14}R^{15}C=N—$) moiety constituting the optically active compound of Formula (VI) (optically active α-amino acid derivative) obtained by the above-described method is first hydrolyzed under acidic conditions (imine acidic-hydrolysis process). Examples of the acids used in the imine acidic-hydrolysis process include inorganic acids (e.g., hydrochloric acid or phosphoric acid) and organic acids including tribasic acids (e.g., acetic acid, citric acid, p-toluenesulfonic acid). More specifically, the imine acidic-hydrolysis process proceeds by treating the compound of Formula (VI) in a suitable medium (e.g., tetrahydrofuran or toluene) at a suitable temperature (e.g., room temperature) using an aqueous solution of the acid. As a result, an ester derivative of amino acid in which the terminal amino group is liberated can be obtained as an imine acidic-hydrolysis product.

Next, if necessary, the ester derivative of the amino acid (acidic-hydrolysis product) obtained above is subjected to a hydrolysis reaction under conditions more acidic than the imine acidic-hydrolysis or under basic conditions. Thus, a desired amino acid in which the terminal of the acidic-hydrolysis product (i.e., the ester group (—$CO_2R^{17}$) constituting the imine acidic-hydrolysis product) has become a carboxylic acid can be obtained.

Alternatively, in the second method, a process in the opposite order relative to that of the method described above is adopted. That is to say, the ester group (—$CO_2R^{17}$) constituting the optically active compound of Formula (VI) (optically active α-amino acid derivative) obtained by the alkylation reaction described above is first hydrolyzed under basic conditions (ester basic-hydrolysis process). An aqueous alkali solution, such as aqueous sodium hydroxide solution, can be used in this ester basic-hydrolysis process. By such hydrolysis, an ester basic-hydrolysis product in which the terminal of the compound of Formula (VI) (that is, the ester group (—$CO_2R^{17}$) constituting the compound of Formula (VI)) has become a carboxylic acid can be obtained.

Next, the imino group ($R^{14}R^{15}C=N—$) moiety of the above-obtained basic-hydrolysis product is hydrolyzed under acidic conditions (imine acidic-hydrolysis process). Examples of the acids used in the imine acidic-hydrolysis process include inorganic acids (e.g., hydrochloric acid, phosphoric acid, sulfuric acid) and organic acids including tribasic acids (e.g., acetic acid, citric acid). More specifically, the imine acidic-hydrolysis process proceeds by treating the ester basic-hydrolysis product in a suitable medium (e.g., tetrahydrofuran or toluene) at a suitable temperature (e.g., room temperature) using an aqueous solution of the acid described above. As a result, a desired amino acid in which the terminal amino group is liberated can be obtained.

In the present invention, in the case where an amino acid is produced from the compound of Formula (VI), either the first method or the second method may be used, and either method can be selected arbitrarily by those skilled in the art according to the specific structure of the amino acid to be actually produced and other relevant production conditions.

Thus, it is possible to produce a desired optically active α-amino acid, efficiently and as one chooses, without limitations on its structure.

EXAMPLES

Hereinafter, the present invention will be specifically described by way of examples, but is not limited thereto.

In the following examples, unless described otherwise, measurements were carried out under the following conditions.

The infrared (IR) spectrum was recorded using an IR Prestage-21 spectrometer manufactured by Shimadzu Corporation.

The $^1H$ and $^{13}C$ NMR spectra were measured using a JEOL JUM-FX400 NMR apparatus manufactured by JEOL Ltd. (400 MHz in $^1H$ NMR and 100 MHz in $^{13}C$ NMR) at room temperature. Unless described otherwise, calibration was performed using the center lines of $Si(CH_3)_4$ (δ=0 ppm) and $CDCl_3$ triplet (δ=77 ppm) as the internal standard. The multiplicity was indicated using the following symbols: s=singlet; d=doublet; t=triplet; q=quartet; m=multiplet; and br=broad.

High-performance liquid chromatography (HPLC) was performed with a Shimadzu 10A instrument manufactured by Shimadzu Corporation using a Daicel CHIRALPAK OD or OD-H 4.6 mm×25 mm column manufactured by DAICEL CHEMICAL INDUSTRIES, LTD.

High resolution mass spectrometry (HRMS) was performed using a BRUKER micrOTOF focus-KR manufactured by Bruker.

The optical rotation was measured using a JASCO DIP-1000 digital polarimeter manufactured by JASCO Corporation.

All reactions were monitored by thin layer chromatography (TLC). In the TLC, a silica gel plate (thickness: 0.25 mm, 60F-254) manufactured by Merck was used, and visualization was performed using 254 nm UV light or a dye such as $KMnO_4$, phosphomolybdic acid (PMA) and $CeSO_4$. The product was purified by flash column chromatography using silica gel 60 (1.09386.9025 manufactured by Merck, 230 to 400 mesh).

Example 1

Synthesis of (S)-2,2'-dimethoxy-6,6'-dimethylbutyl phenyl (6)

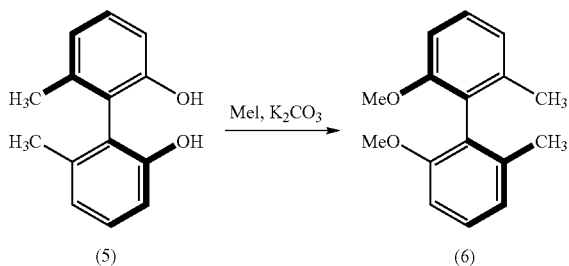

Methyl iodide (0.52 mL, 8.3 mmol) and K$_2$CO$_3$ (0.57 mg, 4.2 mmol) were added to a solution of (S)-6,6'-dimethylbiphenyl-2,2'-diol (5) (89 mg, 0.42 mmol) in acetone (5.0 ml). After being stirred at room temperature for 5 hours, the obtained mixture was filtered through a celite pad with ethyl acetate. The filtrate was concentrated to obtain a residue. The residue was purified by silica gel column chromatography (hexane/ethyl acetate) to give the title compound (6) (105 mg, quantitative).

The physical property data of the obtained compound (6) is shown in Table 1.

TABLE 1

| Physical property data of compound (6) |
|---|
| $[\alpha]^{32}_D$ −38 (c 0.60, CHCl$_3$); $^1$H NMR δ7.21 (t, J = 8 Hz, 2H), 6.89 (d, J = 8 Hz, 2H), 6.79 (d, J = 8 Hz, 2H), 3.65 (s, 6H), 1.93 (s, 6H); $^{13}$C NMR δ156.9, 138.1, 127.8, 126.1, 122.1, 108.2, 55.6, 19.5; IR (neat) 2941, 1579, 1466, 1252, 1080, 777, 743 cm$^{-1}$; HRMS (ESI) Calculated for C$_{16}$H$_{19}$O$_2$ 243.1380 ([M + H$^+$]), Found: 243.1383 ([M + H$^+$]). |

Example 2

Synthesis of (S)-3,3'-dibromo-6,6'-dimethoxy-2,2'-dimethyl-biphenyl (7)

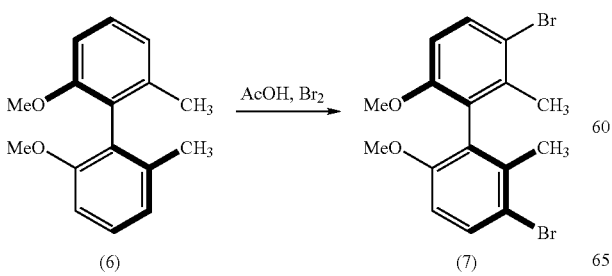

Acetic acid (0.005 mL, 0.083 mmol) and Br$_2$ (0.45 mL, 0.87 mmol) were successively added to a solution of (S)-2, 2'-dimethoxy-6,6'-dimethylbiphenyl (6) (105 mg, 0.415 mmol) obtained in Example 1 in CH$_2$Cl$_2$ (4.0 mL). The obtained solution was stirred at room temperature for 1 hour, and poured into an ice-cold saturated NaHCO$_3$ aqueous solution. The organic phase was separated, and the aqueous phase was extracted twice with ethyl acetate. The combined extract was dried over Na$_2$SO$_4$ and concentrated to obtain a residual oil. The oil was purified by silica gel column chromatography (hexane/ethyl acetate) to give the title compound (7) (161 mg, 97%).

The physical property data of the obtained compound (7) is shown in Table 2.

TABLE 2

| Physical property data of compound (7) |
|---|
| $[\alpha]^{32}_D$ −36 (c 0.68, CHCl$_3$); $^1$H NMR δ7.49 (d, J = 9 Hz, 2H), 6.68 (d, J = 8 Hz, 2H), 3.63 (s, 6H), 1.99 (s, 6H); $^{13}$C NMR δ156.0, 137.3, 131.9, 127.6, 116.3, 109.9, 55.8, 20.0; IR (neat) 2934, 2359, 1566, 146, 1429, 1281, 1254, 1080, 1230, 799 cm$^{-1}$; HRMS (ESI) Calculated for C$_{16}$H$_{16}$Br$_2$O$_2$ 397.9512 ([M$^+$]), Found: 397.9500 ([M$^+$]). |

Example 3

Synthesis of (S)-3,3'-di(3,4,5-trifluorophenyl)-6,6'-dimethoxy-2,2'-dimethylbiphenyl (8)

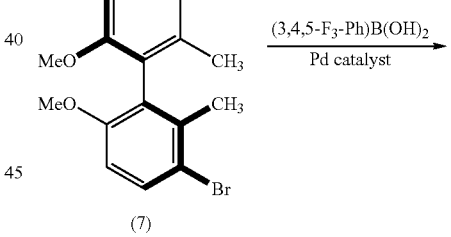

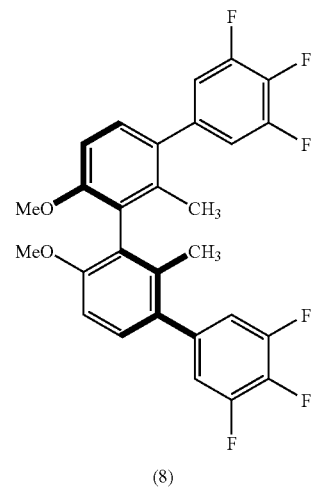

First, 3,4,5-trifluorophenylboronic acid (868 mg, 5.50 mmol), Pd(OAc)$_2$ (62 mg, 0.28 mmol), P(o-tolyl)$_3$ (P(o-Tol)$_3$: 335 mg, 1.10 mmol), and K$_3$PO$_4$-nH$_2$O (3.93 g, 13.8 mmol) were successively added to a solution of (S)-3,3'-dibromo-6,6'-dimethoxy-2,2'-dimethylbiphenyl (7) (550 mg, 1.37 mmol) obtained in Example 2 in dry DMF (16 mL). After being refluxed under an argon atmosphere overnight, the obtained mixture was filtered through a celite pad with diethyl ether. The filtrate was poured into a mixture of H$_2$O and diethyl ether with vigorous stirring. The organic phase was separated, and the aqueous phase was extracted twice with diethyl ether. The combined extract was dried over Na$_2$SO$_4$ and concentrated to obtain a residue. The residue was purified by silica gel column chromatography (hexane/ethyl acetate) to give the title compound (8) in a quantitative yield.

The physical property data of the obtained compound (8) is shown in Table 3.

TABLE 3

Physical property data of compound (8)

$[\alpha]^{32}_D$ −8 (c 0.43, CHCl$_3$); $^1$H NMR δ7.18 (d, J = 8 Hz, 2H), 6.97 (t, J = 8 8 Hz, 4H), 6.90 (d, J = 8 Hz, 2H), 3.76 (s, 6H), 1.86 (s, 6H); $^{13}$C NMR δ156.7, 150.7 (ddd, J$_{C-F}$ = 250, 10, 4 Hz), 138.6 (dt, J$_{C-F}$ = 251, 5 Hz), 138.4 (dt, J$_{C-F}$ = 8, 5 Hz), 135.2, 132.2, 129.6, 126.9, 113.7 (dd, J$_{C-F}$ = 16, 6 Hz), 108.4, 55.7, 17.4; IR (neat) 2940, 1614, 1516, 1477, 1261, 1244, 1084, 1042, 806, 754 cm$^{-1}$; HRMS (ESI) Calculated for C$_{28}$H$_{20}$F$_6$O$_2$ 502.1362 ([M$^+$]), Found: 502.1381 ([M$^+$]).

Example 4

Synthesis of (S)-2,2'-bis(bromomethyl)-6,6'-dimethoxy-3,3'-di(3,4,5-trifluorophenyl) biphenyl (9)

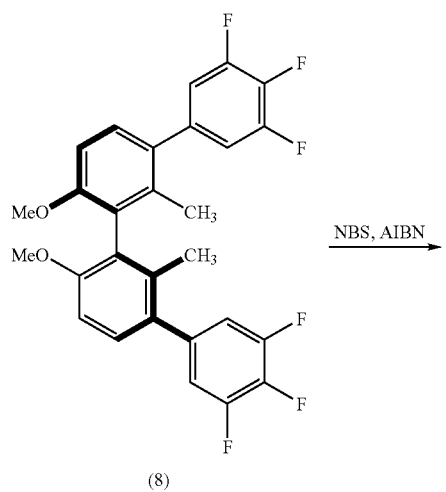

(8)

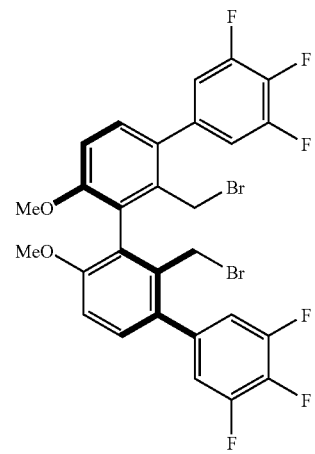

(9)

N-Bromosuccinimide (611 mg, 3.43 mmol) and 2,2'-azobisisobutyronitrile (AIBN) (23 mg, 0.14 mmol) were successively added to a solution of (S)-3,3'-di(3,4,5-trifluorophenyl)-6,6'-dimethoxy-2,2'-dimethylbiphenyl (8) (690 mg, 1.37 mmol) obtained in Example 3 in benzene (10 mL). After being refluxed for 1.5 hours, the mixture was cooled to room temperature and filtered through a celite pad using diethyl ether. The filtrate was concentrated to obtain a residue. The residue was purified by silica gel column chromatography (hexane/diethyl ether) to give the title compound (9) (820 mg, 91%).

The physical property data of the obtained compound (9) is shown in Table 4.

TABLE 4

Physical property data of compound (9)

$[\alpha]^{32}_D$ +51 (c 0.40, CHCl$_3$); $^1$H NMR δ7.26 (d, J = 9 Hz, 2H), 7.16 (d, J = 8 Hz, 4H), 7.04 (d, J = 8 Hz, 2H), 4.08 (s, 4H), 3.77 (s, 6H); $^{13}$C NMR δ157.0, 150.7 (ddd, J$_{C-F}$ = 251, 10, 5 Hz), 139.1 (dt, J$_{C-F}$ = 253, 15 Hz), 136.4 (dt, J$_{C-F}$ = 8, 5 Hz), 132.8, 131.3, 125.5, 113.8 (dd, J$_{C-F}$ = 16, 6 Hz), 111.2, 55.7, 30.1; IR (neat) 2940, 1614, 1526, 1477, 1435, 1271, 1043, 816, 758 cm$^{-1}$; HRMS (ESI) Calculated for C$_{28}$H$_{18}$Br$_2$F$_6$O$_2$ 657.9572 ([M$^+$]), Found: 657.9571 ([M$^+$]).

Example 5

Synthesis of chiral ammonium salt ((S)-4a)

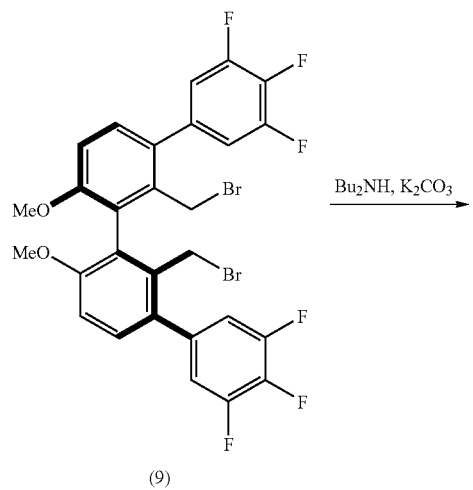

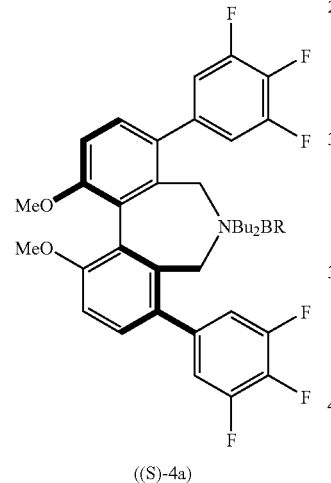

Bu$_2$NH (0.74 mL, 0.43 mmol) and K$_2$CO$_3$ (0.60 mg, 4.4 mmol) were added to a solution of (S)-2,2'-bis(bromomethyl)-6,6'-dimethoxy-3,3'-di(3,4,5-trifluorophenyl) biphenyl (9) (316 mg, 0.48 mmol) obtained in Example 4 in acetonitrile (5 mL). After being stirred at 85° C. overnight, the obtained mixture was cooled to room temperature and filtered through a celite pad using CH$_2$Cl$_2$. The filtrate was concentrated to obtain a residue. The residue was purified by silica gel column chromatography (CH$_2$Cl$_2$/CH$_3$OH) to give the title compound chiral ammonium salt ((S)-4a) in the form of a white solid (290 mg, 94%).

The physical property data of the obtained chiral ammonium salt ((S)-4a) is shown in Table 5.

TABLE 5

Physical property data of chiral ammonium salt ((S)-4a)

[α]$^{32}_D$ −63 (c 0.37, CHCl$_3$); $^1$H NMR δ7.41 (d, J = 9 Hz, 2H), 7.23 (d, J = 9 Hz, 2H), 7.14 (br s, 4H), 4.74 (d, J = 14 Hz, 2H), 3.90 (s, 6H), 3.66 (d, J = 14 Hz, 2H), 3.18 (t, J = 13 Hz, 2H), 2.65-2.80 (m, 2H), 0.90-1.18 (m, 6H), 0.73 (t, J = 7 Hz, 6H),

TABLE 5-continued

Physical property data of chiral ammonium salt ((S)-4a)

0.20--0.38 (m, 2H); $^{13}$C NMR δ156.9, 151.6-152.4 (m), 149.2-149.8 (m), 139.3 (dt, J$_{C-F}$ = 255, 16 Hz), 134.8 (dt, J$_{C-F}$ = 16, 4 Hz), 132.5, 131.9, 126.3, 125.0, 113.5-115.5 (m), 113.3, 57.1, 56.9, 55.8, 24.2, 19.0, 12.9; IR (neat) 3400, 2965, 1614, 1528, 1489, 1287, 1045, 733 cm$^{-1}$; HRMS (ESI) Calculated for C$_{36}$H$_{36}$F$_6$NO$_2$ 628.2645 ([M$^+$]), Found: 628.2642 ([M$^+$]).

Example 6

Synthesis of Chiral Ammonium Salt ((S)-4-b)

(S)-2,2'-Diisopropoxy-6,6'-dimethylbutyl phenyl was synthesized in the same manner as in Example 1, except that isopropyl iodide (0.81 mL, 8.3 mmol) was used instead of the methyl iodide used in Example 1. Then, treatment as in Examples 2 to 5 was performed using the (S)-2,2'-diisopropoxy-6,6'-dimethylbutyl phenyl instead of the compound (6) obtained in Example 1, to give the following chiral ammonium salt ((S)-4-b) (250 mg, 78%).

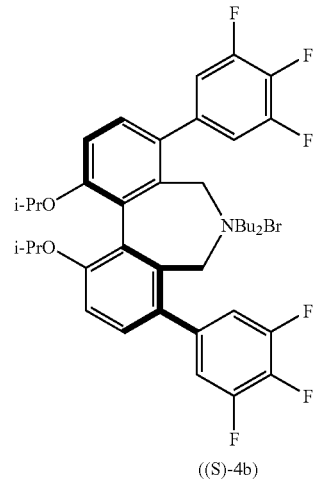

The physical property data of the obtained chiral ammonium salt ((S)-4-b) is shown in Table 6.

TABLE 6

Physical property data of chiral ammonium salt ((S)-4b)

$^1$H NMR δ7.35 (d, J = 9 Hz, 2H), 7.14 (d, J = 9 Hz, 2H), 4.76 (d, J = 14 Hz, 2H), 4.56 (m, 2H), 3.60 (d, J = 14 Hz, 2H), 3.23 (t, J = 13 Hz, 2H), 2.65-2.76 (m, 2H), 1.40 (d, J = 6 Hz, 6H), 1.22 (d, J = 6 Hz, 6H), 0.94-1.10 (m, 6H), 0.73 (t, J = 7 Hz, 6H), 0.29 (m, 2H)

Example 7

Synthesis of (S)-3,3',5,5'-tetrabromo-6,6'-dimethylbiphenyl-2,2'-diol (10)

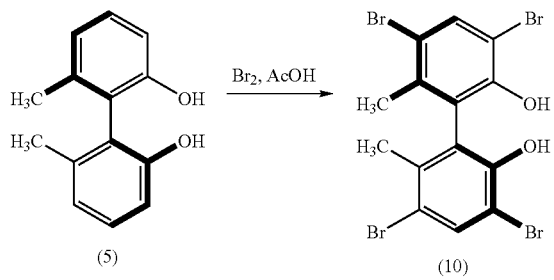

Acetic acid (0.006 mL, 0.10 mmol) and $Br_2$ (0.11 mL, 2.10 mmol) were successively added to a solution of (S)-6,6'-dimethylbiphenyl-2,2'-diol (5) (110 mg, 0.51 mmol) in $CH_2Cl_2$ (5.0 mL). After being stirred at room temperature for 40 minutes, the obtained solution was poured into a mixture of $H_2O$ and $CH_2Cl_2$ with vigorous stirring. The organic layer was separated, and the aqueous layer was extracted twice with $CH_2Cl_2$. The combined extract was dried over $Na_2SO_4$ and concentrated to obtain a residual solid. The solid was purified by silica gel column chromatography (hexane/ethyl acetate) to give the title compound (10) (236 mg, 87%).

The physical property data of the obtained compound (10) is shown in Table 7.

TABLE 7

Physical property data of compound (10)

$[\alpha]^{32}_D$ −38 (c 0.50, $CHCl_3$); $^1H$ NMR δ7.75 (s, 2H), 5.35 (s, 2H), 2.03 (s, 6H); $^{13}C$ NMR δ149.0, 137.8, 134.7, 124.5, 116.1, 107.9, 20.0; IR (neat) 3501, 1425, 1287, 1211, 1061, 1032, 758, 675 $cm^{-1}$; HRMS (ESI) Calculated for $C_{14}H_9Br_4O_2$ 524.7331 ([M − H]$^-$), Found: 524.7337 ([M − H]$^-$).

Example 8

Synthesis of (S)-3,3',5,5'-tetrabromo-2,2'-dimethoxy-6,6'-dimethylbiphenyl (11)

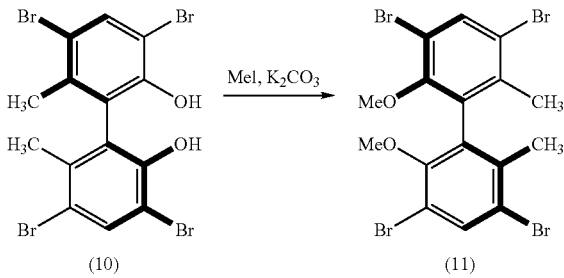

Methyl iodide (0.56 mL, 8.9 mmol) and $K_2CO_3$ (0.62 mg, 4.45 mmol) were added to a solution of (S)-3,3',5,5'-tetrabromo-6,6'-dimethylbiphenyl-2,2'-diol (10) (236 mg, 0.45 mmol) obtained in Example 7 in acetone (10 mL). After being stirred at room temperature for 2 hours, the obtained mixture was filtered through a celite pad using ethyl acetate. The filtrate was concentrated to obtain a residue. The residue was purified by silica gel column chromatography (hexane/ethyl acetate) to give the title compound (II) (246 mg, 98%).

The physical property data of the obtained compound (II) is shown in Table 8.

TABLE 8

Physical property data of compound (11)

$[\alpha]^{32}_D$ +7 (c 0.64, $CHCl_3$); $^1H$ NMR δ7.84 (s, 2H), 3.54 (s, 6H), 2.03 (s, 6H); $^{13}C$ NMR δ153.8, 136.8, 136.0, 133.6, 120.3, 115.0, 60.5, 20.5; IR (neat) 2938, 1452, 1406, 1350, 1260, 1063, 930, 866 $cm^{-1}$; HRMS (ESI) Calculated for $C_{16}H_{14}Br_4O_2$ 553.7722 ([M$^+$]), Found: 553.7718 ([M$^+$]).

Example 9

Synthesis of (S)-3,3',5,5'-tetra(3,4,5-trifluorophenyl)-2,2'-dimethoxy-6,6'-dimethylbiphenyl (12)

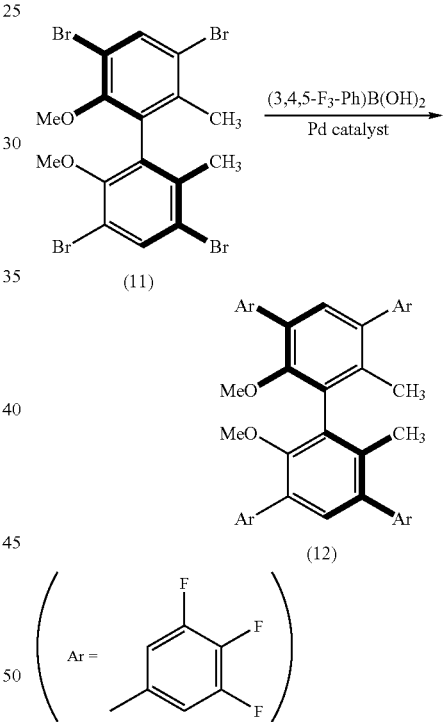

First, 3,4,5-trifluorophenylboronic acid (718 mg, 4.55 mmol), $Pd(OAc)_2$ (34 mg, 0.15 mmol), $P(o-Tol)_3$ (185 mg, 0.61 mmol) and $K_3PO_4 \cdot nH_2O$ (2.17 g, 7.58 mmol) were successively added to a solution of (S)-3,3',5,5'-tetrabromo-2,2'-dimethoxy-6,6'-dimethylbiphenyl (11) (423 mg, 0.76 mmol) obtained in Example 8 in dry DMF (10 mL). After being refluxed under an argon atmosphere for 20 hours, the obtained mixture was filtered through a celite pad using diethyl ether. The filtrate was poured into a mixture of $H_2O$ and diethyl ether with vigorous stirring. The combined extract was dried over $Na_2SO_4$ and concentrated to obtain a residue. The residue was purified by silica gel column chromatography (hexane/diethyl ether) to give the title compound (12) (377 mg, 65%).

The physical property data of the obtained compound (12) is shown in Table 9.

TABLE 9

Physical property data of compound (12)

[α]$^{34}_D$ +17 (c 0.15, CHCl$_3$); $^1$H NMR δ7.28 (d, J = 8 Hz, 2H), 7.29 (d, J = 9 Hz, 2H), 7.20 (s, 2H), 7.00 (d, J = 8 Hz, 2H), 6.98 (d, J = 8 Hz, 2H), 3.31 (s, 6H), 1.98 (s, 6H); $^{13}$C NMR δ154.8, 151.1 (ddd, J$_{C-F}$ = 251, 10, 4 Hz), 138.8 (ddt, J$_{C-F}$ = 254, 16, 4 Hz), 136.1, 135.65, 135.56 (ddt, J$_{C-F}$ = 316, 8, 5 Hz), 132.8, 131.2, 129.4, 113.4 (ddd, J$_{C-F}$ = 58, 16, 6 Hz), 60.4, 18.1; IR (neat) 2930, 2359, 1614, 1526, 1470, 1418, 1395, 1258, 1098, 860, 732 cm$^{-1}$; HRMS (ESI) Calculated for C$_{40}$H$_{22}$F$_{12}$O$_2$ 762.1423 ([M$^+$]), Found: 762.1424 ([M$^+$]).

Example 10

Synthesis of Chiral Ammonium Salt ((S)-5)

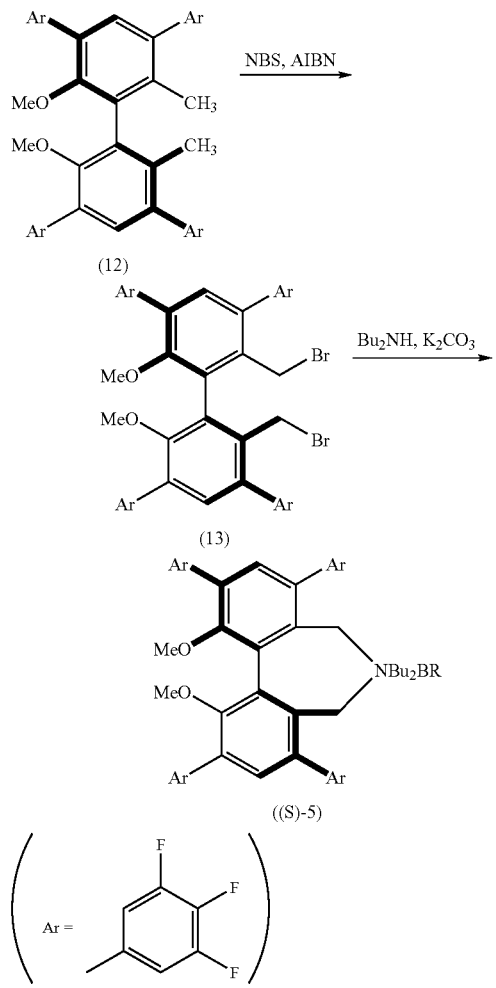

N-Bromosuccinimide (203 mg, 1.14 mmol) and 2,2'-azobisisobutyronitrile (AIBN) (8 mg, 0.049 mmol) were successively added to a solution of (S)-3,3',5,5'-tetra(3,4,5-trifluorophenyl)-2,2'-dimethoxy-6,6'-dimethylbiphenyl (12) (377 mg, 0.49 mmol) obtained in Example 9 in benzene (5.0 mL). After being refluxed for 30 min, the mixture was cooled to room temperature and filtered through a celite pad using diethyl ether. The filtrate was concentrated to obtain the compound (13) as a residual solid. This compound was used in the following reaction without further purification.

Bu$_2$NH (0.051 mL, 0.30 mmol) and K$_2$CO$_3$ (410 mg, 2.96 mmol) were added to a solution of the thus obtained crude product (compound (13)) in acetonitrile (5 mL). After being stirred at 95° C. for 10 hours, the obtained mixture was cooled to room temperature and filtered through a celite pad using CH$_2$Cl$_2$. The filtrate was concentrated to obtain a residue. The residue was purified by silica gel chromatography (CH$_2$Cl$_2$/methanol) to give the chiral ammonium salt ((S)-5) in the form of a white solid (254 mg, 53% after two processes).

The physical property data of the obtained chiral ammonium salt ((S)-5) is shown in Table 10.

TABLE 10

Physical property data of chiral ammonium salt ((S)-5)

[α]$^{34}_D$ −34 (c 0.48, CHCl$_3$); $^1$H NMR δ7.20-7.60 (m, 10H), 4.73 (d, J = 14 Hz, 2H), 4.05 (d, J = 14 Hz, 2H), 3.41 (s, 6H), 3.08 (t, J = 12 Hz, 1H), 2.85 (t, J = 12 Hz, 2H), 0.85-1.20 (m, 6H), 0.73 (t, J = 7 Hz, 6H), 0.30 (br s, 2H); $^{13}$C NMR δ156.0, 151.2 (ddd, J$_{C-F}$ = 251, 9, 3 Hz), 139.8 (dq, J$_{C-F}$ = 256, 15 Hz), 136.6, 134.7, 134.1-134.6 (m), 133.8, 132.5-133.0 (m), 113.6 (dd, J$_{C-F}$ = 16, 6 Hz), 61.8, 57.5, 24.4, 19.4, 13.2; IR (neat) 3404, 2965, 2357, 1616, 1528, 1472, 1398, 1260, 1242, 1045, 862 cm$^{-1}$; HRMS (ESI) Calculated for C$_{48}$H$_{38}$F$_{12}$NO$_2$ 880.2705 ([M$^+$]), Found: 880.2703 ([M$^+$]).

Example 11

Confirmation of α-Benzylation of Glycine (A1)

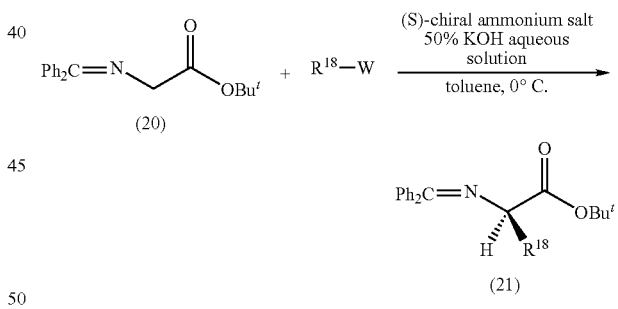

A mixture of the chiral ammonium salt ((S)-4a) (1 mol %; phase-transfer catalyst) obtained in Example 5 and benzyl bromide (3 equivalents) as the compound represented by R$^{18}$—W in the above formula was added to a mixture of 50% KOH aqueous solution (1 mL) and a toluene solution (1.5 mL) of N-(biphenylmethylene)glycine tert-butyl ester (20) (88.6 mg, 0.3 mmol), and the resultant was stirred vigorously under an argon atmosphere at 0° C. for 5 hours. Completion of the reaction was confirmed by TLC, and then the mixture was poured into water and extracted with ether. The organic extract was washed with brine and dried over Na$_2$SO$_4$. The solvent was evaporated under reduced pressure, and then the residual oil was purified by silica gel column chromatography (ether/hexane=1/10 as the eluent) to give the corresponding compound (21) ((R)-tert-butyl N-(diphenylmethylene) phenylalanine) (yield 96%). The optical purity of the compound

(21) obtained in this example was analyzed by HPLC (Daicel Chiralcel OD, eluent: hexane/2-propanol=100/1, flow rate: 0.5 mL/min, retention time: (R)-form=14.8 min and (S)-form=28.2 min). The optical purity of the compound (21) obtained in this example is shown in Table 11.

Example 12

Confirmation of α-Benzylation of Glycine (A2)

The compound (21) was obtained in a quantitative yield in the same manner as in Example 11, except that the reaction temperature was set to room temperature instead of 0° C., and the reaction time was set to 3 hours instead of 5 hours. The optical purity of the compound (21) obtained in this example is shown in Table 11.

Example 13

Confirmation of α-Benzylation of Glycine (A3)

The compound (21) was obtained (yield 95%) in the same manner as in Example 11, except that the chiral ammonium salt ((S)-4-b) (1 mol %) obtained in Example 6 was used instead of the chiral ammonium salt ((S)-4a) obtained in Example 5 as the phase-transfer catalyst, and the reaction time was set to 4 hours instead of 5 hours. The optical purity of the compound (21) obtained in this example is shown in Table 11.

Example 14

Confirmation of α-Benzylation of Glycine (A4)

The compound (21) was obtained (yield 92%) in the same manner as in Example 11, except that the chiral ammonium salt ((S)-4-b) (1 mol %) obtained in Example 6 was used instead of the chiral ammonium salt ((S)-4a) obtained in Example 5 as the phase-transfer catalyst, the reaction temperature was set to room temperature instead of 0° C., and the reaction time was set to 2.5 hours instead of 5 hours. The optical purity of the compound (21) obtained in this example is shown in Table 11.

Example 15

Confirmation of α-Benzylation of Glycine (A5)

The compound (21) was obtained (yield 82%) in the same manner as in Example 11, except that the chiral ammonium salt ((S)-5) (1 mol %) obtained in Example 10 was used instead of the chiral ammonium salt ((S)-4a) obtained in Example 5 as the phase-transfer catalyst, and the reaction time was set to 10 hours instead of 5 hours. It was confirmed by TLC that part of the starting material remained. The optical purity of the compound (21) obtained in this example is shown in Table 11.

Example 16

Confirmation of α-Benzylation of Glycine (A6)

The compound (21) was obtained (yield 96%) in the same manner as in Example 11, except that the chiral ammonium salt ((S)-5) (1 mol %) obtained in Example 10 was used instead of the chiral ammonium salt ((S)-4a) obtained in Example 5 as the phase-transfer catalyst, the reaction temperature was set to room temperature instead of 0° C., and the reaction time was set to 2.5 hours instead of 5 hours. The optical purity of the compound (21) obtained in this example is shown in Table 11.

TABLE 11

| | Phase-transfer catalyst | Reaction condition | Yield (%) | Optical purity (% ee), (Absolute configuration) |
|---|---|---|---|---|
| Example 11 | (S)-4a | 0° C., 5 hours | 97 | 96, (R) |
| Example 12 | (S)-4a | Room temperature, 3 hours | quantitative | 91, (R) |
| Example 13 | (S)-4b | 0° C., 4 hours | 95 | 86, (R) |
| Example 14 | (S)-4b | Room temperature, 2.5 hours | 92 | 68, (R) |
| Example 15 | (S)-5 | 0° C., 10 hours | 82 | 90, (R) |
| Example 16 | (S)-5 | Room temperature, 2.5 hours | 96 | 98, (R) |

As shown in Table 11, it is found that all compounds (chiral ammonium salts) contained in Formula (I) of the present invention contribute to the α-benzylation of glycine as a phase-transfer catalyst. It is found that, in particular, when the reaction conditions are adjusted, the yield and the optical purity of the product are significantly improved, which is useful in the production of optically active α-amino acid derivatives and optically active α-amino acids using these compounds.

Example 17

Confirmation of α-Benzylation of Glycine (B1)

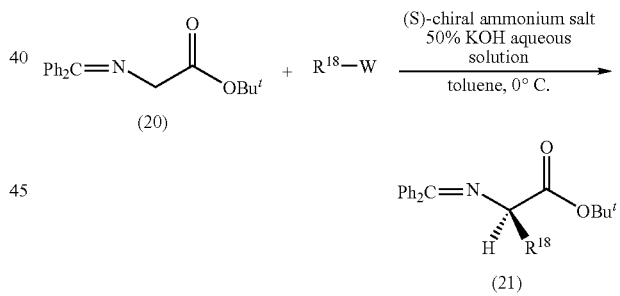

A mixture of the chiral ammonium salt ((S)-4a) obtained in Example 5 (1 mol %; phase-transfer catalyst) and ethyl iodide (8 equivalents) as the compound represented by $R^{18}$—W in the above formula was added to a mixture of 50% KOH aqueous solution (1 mL) and a toluene solution (1.5 mL) of N-(biphenylmethylene)glycine tert-butyl ester (20) (88.6 mg, 0.3 mmol), and the resultant was stirred vigorously under an argon atmosphere at 0° C. for 8 hours. Completion of the reaction was confirmed by TLC, and then the mixture was poured into water and extracted with ether. The organic extract was washed with brine and dried over $Na_2SO_4$. The solvent was evaporated under reduced pressure, and then a residual oil was purified by silica gel column chromatography (ether/hexane=1/10 as the eluent) to give the corresponding compound (21) ((R)-tert-butyl N-(diphenylmethylene) phenylalanine) (yield 92%). The optical purity of the compound (21) obtained in this example was analyzed by HPLC (Daicel Chiralcel OD, eluent: hexane/2-propanol=100/1). The optical purity of the compound (21) obtained in this example is shown in Table 12.

Example 18

Confirmation of α-Benzylation of Glycine (B2)

The compound (21) was obtained (yield 90%) in the same manner as in Example 17, except that allyl bromide (3 equivalents) was used instead of ethyl iodide as the compound represented by $R^{18}$—W in the above formula, and the reaction time was set to 2.5 hours instead of 8 hours. The optical purity of the compound (21) obtained in this example is shown in Table 12.

Example 19

Confirmation of α-Benzylation of Glycine (B3)

The compound (21) was obtained (yield 82%) in the same manner as in Example 17, except that propargyl bromide (3 equivalents) was used instead of ethyl iodide as the compound represented by $R^{18}$—W in the above formula, and the reaction time was set to 10 hours instead of 8 hours. The optical purity of the compound (21) obtained in this example is shown in Table 12.

Example 20

Confirmation of α-Benzylation of Glycine (B4)

The compound (21) was obtained (yield 94%) in the same manner as in Example 17, except that the chiral ammonium salt ((S)-5) (1 mol %) obtained in Example 10 was used instead of the chiral ammonium salt ((S)-4a) obtained in Example 5 as the phase-transfer catalyst, benzyl bromide (1.5 equivalents) was used instead of ethyl iodide as the compound represented by $R^{18}$—W in the above formula, and the reaction time was set to 4 hours instead of 8 hours. The optical purity of the compound (21) obtained in this example is shown in Table 12.

Example 21

Confirmation of α-Benzylation of Glycine (B5)

The compound (21) was obtained (yield 94%) in the same manner as in Example 17, except that the chiral ammonium salt ((S)-5) (1 mol %) obtained in Example 10 was used instead of the chiral ammonium salt ((S)-4a) obtained in Example 5 as the phase-transfer catalyst, propargyl bromide (1.5 equivalents) was used instead of ethyl iodide as the compound represented by $R^{18}$—W in the above formula, and the reaction time was set to 3 hours instead of 8 hours. The optical purity of the compound (21) obtained in this example is shown in Table 12.

Example 22

Confirmation of α-Benzylation of Glycine (B6)

The compound (21) was obtained (yield 92%) in the same manner as in Example 17, except that the chiral ammonium salt ((S)-5) (1 mol %) obtained in Example 10 was used instead of the chiral ammonium salt ((S)-4a) obtained in Example 5 as the phase-transfer catalyst, allyl bromide (1.5 equivalents) was used instead of ethyl iodide as the compound represented by $R^{18}$—W in the above formula, and the reaction time was set to 3.5 hours instead of 8 hours. The optical purity of the compound (21) obtained in this example is shown in Table 12.

Example 23

Confirmation of α-Benzylation of Glycine (B7)

The compound (21) was obtained (yield 86%) in the same manner as in Example 17, except that the chiral ammonium salt ((S)-5) (1 mol %) obtained in Example 10 was used instead of the chiral ammonium salt ((S)-4a) obtained in Example 5 as the phase-transfer catalyst, and the reaction time was set to 10 hours instead of 8 hours. The optical purity of the compound (21) obtained in this example is shown in Table 12.

Example 24

Confirmation of α-Benzylation of Glycine (B8)

The compound (21) was obtained (yield 92%) in the same manner as in Example 17, except that the chiral ammonium salt ((S)-5) (0.2 mol %) obtained in Example 10 was used instead of the chiral ammonium salt ((S)-4a) obtained in Example 5 as the phase-transfer catalyst, propargyl bromide (2 equivalents) was used instead of ethyl iodide as the compound represented by $R^{18}$—W in the above formula, the reaction temperature was set to 20° C. instead of 0° C., and the reaction time was set to 6 hours instead of 8 hours. The optical purity of the compound (21) obtained in this example is shown in Table 12.

Example 25

Confirmation of α-Benzylation of Glycine (B9)

The compound (21) was obtained (yield 95%) in the same manner as in Example 17, except that the chiral ammonium salt ((S)-5) (0.5 mol %) obtained in Example 10 was used instead of the chiral ammonium salt ((S)-4a) obtained in Example 5 as the phase-transfer catalyst, allyl bromide (1.5 equivalents) was used instead of ethyl iodide as the compound represented by $R^{18}$—W in the above formula, the reaction temperature was set to 20° C. instead of 0° C., and the reaction time was set to 5 hours instead of 8 hours. The optical purity of the compound (21) obtained in this example is shown in Table 12.

Example 26

Confirmation of α-Benzylation of Glycine (B10)

The compound (21) was obtained (yield 81%) in the same manner as in Example 17, except that the chiral ammonium salt ((S)-5) (1 mol %) obtained in Example 10 was used instead of the chiral ammonium salt ((S)-4a) obtained in Example 5 as the phase-transfer catalyst, the reaction temperature was set to 20° C. instead of 0° C., and the reaction time was set to 10 hours instead of 8 hours. The optical purity of the compound (21) obtained in this example is shown in Table 12.

Example 27

Confirmation of α-Benzylation of Glycine (B11)

The compound (21) was obtained (yield 93%) in the same manner as in Example 17, except that the chiral ammonium salt ((S)-5) (0.5 mol %) obtained in Example 10 was used instead of the chiral ammonium salt ((S)-4a) obtained in Example 5 as the phase-transfer catalyst, benzyl bromide (1.2 equivalents) was used instead of ethyl iodide as the compound represented by $R^{18}$—W in the above formula, the reaction temperature was set to 20° C. instead of 0° C., and the reaction time was set to 5 hours instead of 8 hours. The optical purity of the compound (21) obtained in this example is shown in Table 12.

Example 28

Confirmation of α-Benzylation of Glycine (B12)

The compound (21) was obtained (yield 94%) in the same manner as in Example 17, except that the chiral ammonium salt ((S)-5) (0.1 mol %) obtained in Example 10 was used instead of the chiral ammonium salt ((S)-4a) obtained in Example 5 as the phase-transfer catalyst, benzyl bromide (1.5 equivalents) was used instead of ethyl iodide as the compound represented by $R^{18}$—W in the above formula, the reaction temperature was set to 20° C. instead of 0° C., and the reaction time was set to 12 hours instead of 8 hours. The optical purity of the compound (21) obtained in this example is shown in Table 12.

TABLE 12

| | Phase-transfer catalyst (mol %) | $R^{18}$-W (equivalent) | Reaction condition | Yield (%) | Optical purity (% ee), (Absolute configuration) |
|---|---|---|---|---|---|
| Example 17 | (S)-4a (1) | Ethyl iodide (8) | 0° C., 8 hours | 92 | 81, (R) |
| Example 18 | (S)-4a (1) | Allyl bromide (3) | 0° C., 2.5 hours | 90 | 93, (R) |
| Example 19 | (S)-4a (1) | Propargyl bromide (3) | 0° C., 10 hours | 82 | 90, (R) |
| Example 20 | (S)-5 (1) | Benzyl bromide (1.5) | 0° C., 4 hours | 94 | 86, (R) |
| Example 21 | (S)-5 (1) | Propargyl bromide (1.5) | 0° C., 3 hours | 94 | 87, (R) |
| Example 22 | (S)-5 (1) | Allyl bromide (1.5) | 0° C., 3.5 hours | 92 | 88, (R) |
| Example 23 | (S)-5 (1) | Ethyl iodide (3) | 0° C., 10 hours | 86 | 90, (R) |
| Example 24 | (S)-5 (0.2) | Propargyl bromide (2) | 20° C., 6 hours | 92 | 91, (R) |
| Example 25 | (S)-5 (0.5) | Allyl bromide (1.5) | 20° C., 5 hours | 95 | 93, (R) |
| Example 26 | (S)-5 (1) | Ethyl iodide (3) | 20° C., 10 hours | 81 | 90, (R) |
| Example 27 | (S)-5 (0.5) | Benzyl bromide (1.2) | 20° C., 5 hours | 93 | 95, (R) |
| Example 28 | (S)-5 (0.1) | Benzyl bromide (1.5) | 20° C., 12 hours | 94 | 95, (R) |

As shown in Table 12, it is found that all compounds (chiral ammonium salts) contained in Formula (I) of the present invention contribute to the α-benzylation of glycine as a phase-transfer catalyst. It is found that, in particular, when the type of compound represented by $R^{18}$—W in the above formula, the reaction conditions, and the like are adjusted, the yield and the optical purity of the product are significantly improved, which is useful in the production of optically active α-amino acid derivatives and optically active α-amino acids using these compounds.

INDUSTRIAL APPLICABILITY

According to the present invention, a chiral phase-transfer catalyst having a simpler structure is provided. This phase-transfer catalyst can be produced by a smaller number of process steps than conventional ones, which leads to a reduction in the production cost. Such a phase-transfer catalyst is extremely useful in the synthesis of α-alkyl-α-amino acids and derivatives thereof, and α,α-dialkyl-α-amino acids and derivatives thereof. The amino acids and their derivatives thus synthesized play an important and special role in the design of peptides having enhanced activity (pharmacological or physiological activity, for example), as effective enzyme inhibitors, and as chiral building blocks for the synthesis of compounds having various biological activities. Therefore, they are useful for the development of novel foods and pharmaceuticals.

The invention claimed is:
1. A compound represented by Formula (I) below:

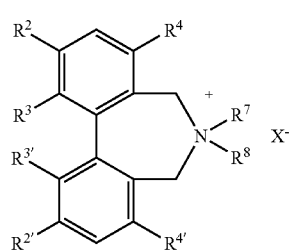

wherein
$R^2$ and $R^{2'}$ are both:
an aryl group, wherein the aryl group may be substituted with at least one group selected from the group consisting of:
a $C_1$ to $C_4$ alkyl group that may be branched if a $C_3$ to $C_4$ alkyl group and that may be substituted with a halogen atom,
a $C_1$ to $C_5$ alkoxy group that may be branched if a $C_3$ to $C_5$ alkoxy group and that may be substituted with a halogen atom,
an aryl group that may be substituted with a halogen atom or a $C_1$ to $C_4$ alkyl group that may be branched if a $C_3$ to $C_4$ alkyl group and that may be substituted with a halogen atom, and
a halogen atom;
$R^3$ and $R^{3'}$ are each independently:
a $C_1$ to $C_5$ alkoxy group that may be substituted with a halogen atom, an aryl group, or a combination thereof, that may be branched or form a cyclic group if a $C_3$ to $C_5$ alkoxy group, or a combination thereof;

R⁴ and R⁴' are each independently a group selected from the group consisting of:
(i) a hydrogen atom;
(ii) a halogen atom;
(iii) a $C_1$ to $C_6$ alkyl group that may be branched or form a cyclic group if a $C_3$ to $C_6$ alkyl group and that may be substituted with a halogen atom;
(iv) a $C_2$ to $C_6$ alkenyl group that may be branched or form a cyclic group if a $C_3$ to $C_6$ alkenyl group and that may be substituted with a halogen atom;
(v) a $C_2$ to $C_6$ alkynyl group that may be branched or form a cyclic group if a $C_3$ to $C_6$ alkynyl group and that may be substituted with a halogen atom;
(vi) an aralkyl group, wherein the aryl moiety constituting the aralkyl group may be substituted with at least one group selected from the group consisting of:
a $C_1$ to $C_4$ alkyl group that may be branched if a $C_3$ to $C_4$ alkyl group and that may be substituted with a halogen atom,
a $C_1$ to $C_5$ alkoxy group that may be branched if a $C_3$ to $C_5$ alkoxy group and that may be substituted with a halogen atom,
an aryl group that may be substituted with a halogen atom or a $C_1$ to $C_4$ alkyl group that may be branched if a $C_3$ to $C_4$ alkyl group and that may be substituted with a halogen atom, and
a halogen atom; and
(vii) an aryl group, wherein the aryl group may be substituted with at least one group selected from the group consisting of:
a $C_1$ to $C_4$ alkyl group that may be branched if a $C_3$ to $C_4$ alkyl group and that may be substituted with a halogen atom,
a $C_1$ to $C_5$ alkoxy group that may be branched if a $C_3$ to $C_5$ alkoxy group and that may be substituted with a halogen atom,
an aryl group that may be substituted with a halogen atom or a $C_1$ to $C_4$ alkyl group that may be branched if a $C_3$ to $C_4$ alkyl group and that may be substituted with a halogen atom, and
a halogen atom;
$R^7$ and $R^8$ are each independently a group selected from the group consisting of:
(i) a $C_1$ to $C_{30}$ alkyl group that may be branched or form a cyclic group if a $C_3$ to $C_{30}$ alkyl group and that may be substituted with a halogen atom;
(ii) a $C_2$ to $C_{12}$ alkenyl group that may be branched or form a cyclic group if a $C_3$ to $C_{12}$ alkenyl group and that may be substituted with a halogen atom;
(iii) a $C_2$ to $C_{12}$ alkynyl group that may be branched or form a cyclic group if a $C_3$ to $C_{12}$ alkynyl group and that may be substituted with a halogen atom; and
(iv) an aryl group, wherein the aryl group may be substituted with at least one group selected from the group consisting of:
a $C_1$ to $C_4$ alkyl group that may be branched if a $C_3$ to $C_4$ alkyl group and that may be substituted with a halogen atom,
a $C_1$ to $C_5$ alkoxy group that may be branched if a $C_3$ to $C_5$ alkoxy group and that may be substituted with a halogen atom,
an aryl group that may be substituted with a halogen atom or a $C_1$ to $C_4$ alkyl group that may be branched if a $C_3$ to $C_4$ alkyl group and that may be substituted with a halogen atom, and
a halogen atom; or $R^7$ and $R^8$ are taken together to form a divalent group selected from the group consisting of:
-$(CH_2)_m$- wherein m is an integer from 2 to 8;

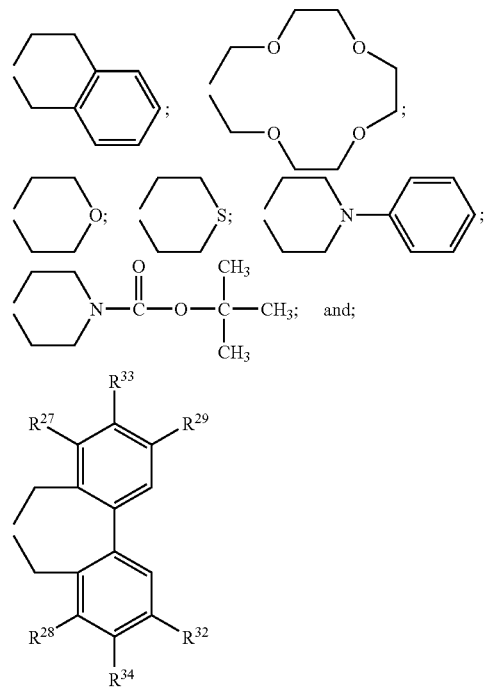

wherein $R^{27}$, $R^{28}$, $R^{29}$, $R^{32}$, $R^{33}$ and $R^{34}$ are each independently a group selected from the group consisting of:
a hydrogen atom;
a $C_1$ to $C_8$ alkyl group that may be branched or form a cyclic group if a $C_3$ to $C_8$ alkyl group, that may be substituted with a halogen atom, or a combination thereof;
a $C_2$ to $C_8$ alkenyl group that may be branched or form a cyclic group if a $C_3$ to $C_8$ alkenyl group, that may be substituted with a halogen atom, or a combination thereof;
a $C_2$ to $C_8$ alkynyl group that may be branched or form a cyclic group if a $C_3$ to $C_8$ alkynyl group, that may be substituted with a halogen atom, or a combination thereof;
an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ wherein $R^{30}$ and $R^{31}$ are each independently a hydrogen atom or a $C_1$ to $C_4$ alkyl group that may be branched if a $C_3$ to $C_4$ alkyl group and that may be substituted with a halogen atom, or a cyclic amino group that is formed by a $C_2$ to $C_8$ alkylene group; and
an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ wherein $R^{30}$ and $R^{31}$ are each independently a hydrogen atom or a $C_1$ to $C_4$ alkyl group that may be branched if a $C_3$ to $C_4$ alkyl group and that may be substituted with a halogen atom, or a cyclic amino group that is formed by a $C_2$ to $C_8$ alkylene group, and $X^-$ is an anion selected from the group consisting of a halide anion, $SCN^-$, $HSO_4^-$, $HF_2^-$, $CF_3SO_3^-$, $CH_3$—$C_6H_4$—$SO_3^-$, and $CH_3SO_3^-$.

2. The compound according to claim 1, wherein $R^4$ and $R^{4'}$ of the compound represented by Formula (I) are both aryl groups, wherein the aryl group may be substituted with at least one group selected from the group consisting of:
- a $C_1$ to $C_4$ alkyl group that may be branched if a $C_3$ to $C_4$ alkyl group and that may be substituted with a halogen atom,
- a $C_1$ to $C_5$ alkoxy group that may be branched if a $C_3$ to $C_5$ alkoxy group and that may be substituted with a halogen atom,
- an aryl group that may be substituted with a halogen atom or a $C_1$ to $C_4$ alkyl group that may be branched if a $C_3$ to $C_4$ alkyl group and that may be substituted with a halogen atom, and
- a halogen atom.

3. A method for producing the compound represented by Formula (I) of claim 1, comprising:
reacting a compound represented by Formula (II) below:

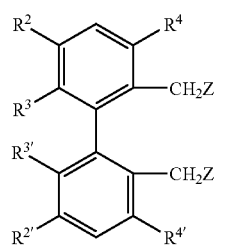

(II)

with a secondary amine represented by Formula (III) below:

(III)

in an organic solvent in the presence of an acid-scavenging agent,
wherein in Formula (II),
$R^2$ and $R^{2'}$ are both:
an aryl group, wherein the aryl group may be substituted with at least one group selected from the group consisting of:
- a $C_1$ to $C_4$ alkyl group that may be branched if a $C_3$ to $C_4$ alkyl group and that may be substituted with a halogen atom,
- a $C_1$ to $C_5$ alkoxy group that may be branched if a $C_3$ to $C_5$ alkoxy group and that may be substituted with a halogen atom,
- an aryl group that may be substituted with a halogen atom or a $C_1$ to $C_4$ alkyl group that may be branched if a $C_3$ to $C_4$ alkyl group and that may be substituted with a halogen atom, and
- a halogen atom;
$R^3$ and $R^{3'}$ are each independently:
a $C_1$ to $C_5$ alkoxy group that may be substituted with a halogen atom, an aryl group, or a combination thereof, that may be branched or form a cyclic group if a $C_3$ to $C_5$ alkoxy group or combination thereof;
$R^4$ and $R^{4'}$ are each independently a group selected from the group consisting of:
(i) a hydrogen atom;
(ii) a halogen atom;
(iii) a $C_1$ to $C_6$ alkyl group that may be branched or form a cyclic group if a $C_3$ to $C_6$ alkyl group and that may be substituted with a halogen atom;
(iv) a $C_2$ to $C_6$ alkenyl group that may be branched or form a cyclic group if a $C_3$ to $C_6$ alkenyl group and that may be substituted with a halogen atom;
(v) a $C_2$ to $C_6$ alkynyl group that may be branched or form a cyclic group if a $C_3$ to $C_6$ alkynyl group and that may be substituted with a halogen atom;
(vi) an aralkyl group, wherein the aryl moiety constituting the aralkyl group may be substituted with at least one group selected from the group consisting of:
- a $C_1$ to $C_4$ alkyl group that may be branched if a $C_3$ to $C_4$ alkyl group and that may be substituted with a halogen atom,
- a $C_1$ to $C_5$ alkoxy group that may be branched if a $C_3$ to $C_5$ alkoxy group and that may be substituted with a halogen atom,
- an aryl group that may be substituted with a halogen atom or a $C_1$ to $C_4$ alkyl group that may be branched if a $C_3$ to $C_4$ alkyl group and that may be substituted with a halogen atom, and
- a halogen atom; and
(vii) an aryl group, wherein the aryl group may be substituted with at least one group selected from the group consisting of:
- a $C_1$ to $C_4$ alkyl group that may be branched if a $C_3$ to $C_4$ alkyl group and that may be substituted with a halogen atom,
- a $C_1$ to $C_5$ alkoxy group that may be branched if a $C_3$ to $C_5$ alkoxy group and that may be substituted with a halogen atom,
- an aryl group that may be substituted with a halogen atom or a $C_1$ to $C_4$ alkyl group that may be branched if a $C_3$ to $C_4$ alkyl group and that may be substituted with a halogen atom, and
- a halogen atom, and Z is a halogen atom, and
in Formula (III),
$R^7$ and $R^8$ are each independently a group selected from the group consisting of:
(i) a $C_1$ to $C_{30}$ alkyl group that may be branched or form a cyclic group if a $C_3$ to $C_{30}$ alkyl group and that may be substituted with a halogen atom;
(ii) a $C_2$ to $C_{12}$ alkenyl group that may be branched or form a cyclic group if a $C_3$ to $C_{12}$ alkenyl group and that may be substituted with a halogen atom;
(iii) a $C_2$ to $C_{12}$ alkynyl group that may be branched or form a cyclic group if a $C_3$ to $C_{12}$ alkynyl group and that may be substituted with a halogen atom; and
(iv) an aryl group, wherein the aryl group may be substituted with at least one group selected from the group consisting of:
- a $C_1$ to $C_4$ alkyl group that may be branched if a $C_3$ to $C_4$ alkyl group and that may be substituted with a halogen atom,
- a $C_1$ to $C_5$ alkoxy group that may be branched if a $C_3$ to $C_5$ alkoxy group and that may be substituted with a halogen atom,
- an aryl group that may be substituted with a halogen atom or a $C_1$ to $C_4$ alkyl group that may be branched if a $C_3$ to $C_4$ alkyl group and that may be substituted with a halogen atom, and
a halogen atom; or
$R^7$ and $R^8$ are taken together to form a divalent group selected from the group consisting of:
—$(CH_2)_m$— wherein m is an integer from 2 to 8;

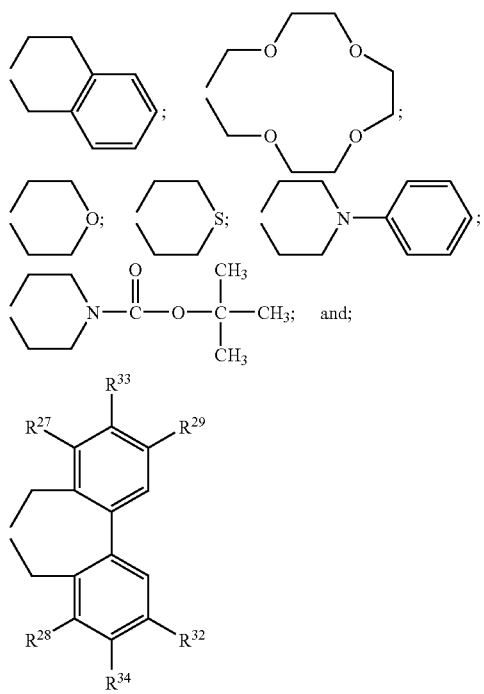

wherein $R^{27}$, $R^{28}$, $R^{29}$, $R^{32}$, $R^{33}$ and $R^{34}$ are each independently a group selected from the group consisting of:
a hydrogen atom;
a $C_1$ to $C_8$ alkyl group that may be branched or form a cyclic group if a $C_3$ to $C_8$ alkyl group, that may be substituted with a halogen atom, or a combination thereof;
a $C_2$ to $C_8$ alkenyl group that may be branched or form a cyclic group if a $C_3$ to $C_8$ alkenyl group, that may be substituted with a halogen atom, or a combination thereof;
a $C_2$ to $C_8$ alkynyl group that may be branched or form a cyclic group if a $C_3$ to $C_8$ alkynyl group, that may be substituted with a halogen atom, or a combination thereof;
an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ wherein $R^{30}$ and $R^{31}$ are each independently a hydrogen atom or a $C_1$ to $C_4$ alkyl group that may be branched if a $C_3$ to $C_4$ alkyl group and that may be substituted with a halogen atom, or a cyclic amino group that is formed by a $C_2$ to $C_8$ alkylene group; and
an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ wherein $R^{30}$ and $R^{31}$ are each independently a hydrogen atom or a $C_1$ to $C_4$ alkyl group that may be branched if a $C_3$ to $C_4$ alkyl group and that may be substituted with a halogen atom, or a cyclic amino group that is formed by a $C_2$ to $C_8$ alkylene group.

4. The method according to claim 3, wherein $R^4$ and $R^{4'}$ of the compound represented by Formula (II) are both aryl groups, wherein the aryl group may be substituted with at least one group selected from the group consisting of:
a $C_1$ to $C_4$ alkyl group that may be branched if a $C_3$ to $C_4$ alkyl group and that may be substituted with a halogen atom,
a $C_1$ to $C_5$ alkoxy group that may be branched if a $C_3$ to $C_5$ alkoxy group and that may be substituted with a halogen atom,
an aryl group that may be substituted with a halogen atom or a $C_1$ to $C_4$ alkyl group that may be branched if a $C_3$ to $C_4$ alkyl group and that may be substituted with a halogen atom, and
a halogen atom.

* * * * *

UNITED STATES PATENT AND TRADEMARK OFFICE
CERTIFICATE OF CORRECTION

Page 1 of 2

PATENT NO. : 8,110,680 B2
APPLICATION NO. : 12/443588
DATED : February 7, 2012
INVENTOR(S) : Keiji Maruoka et al.

It is certified that error appears in the above-identified patent and that said Letters Patent is hereby corrected as shown below:

Under Columns 23 & 24, lines 52-65, please delete;

"
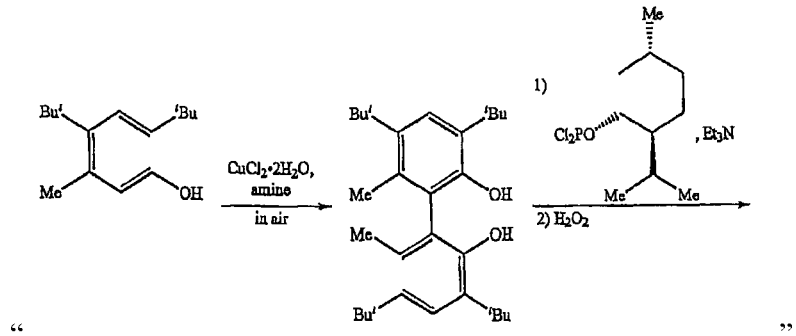
"

Should read

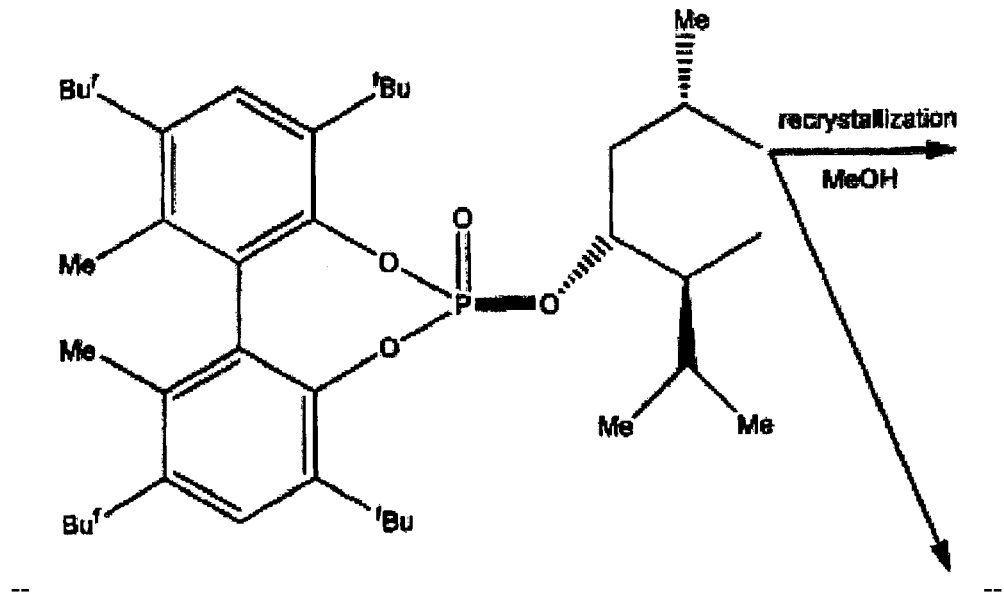

--                                                                --

Signed and Sealed this
Twenty-sixth Day of June, 2012

David J. Kappos
*Director of the United States Patent and Trademark Office*

CERTIFICATE OF CORRECTION (continued)
U.S. Pat. No. 8,110,680 B2

Columns 25 & 26 under -continued, lines 1-32, please delete;

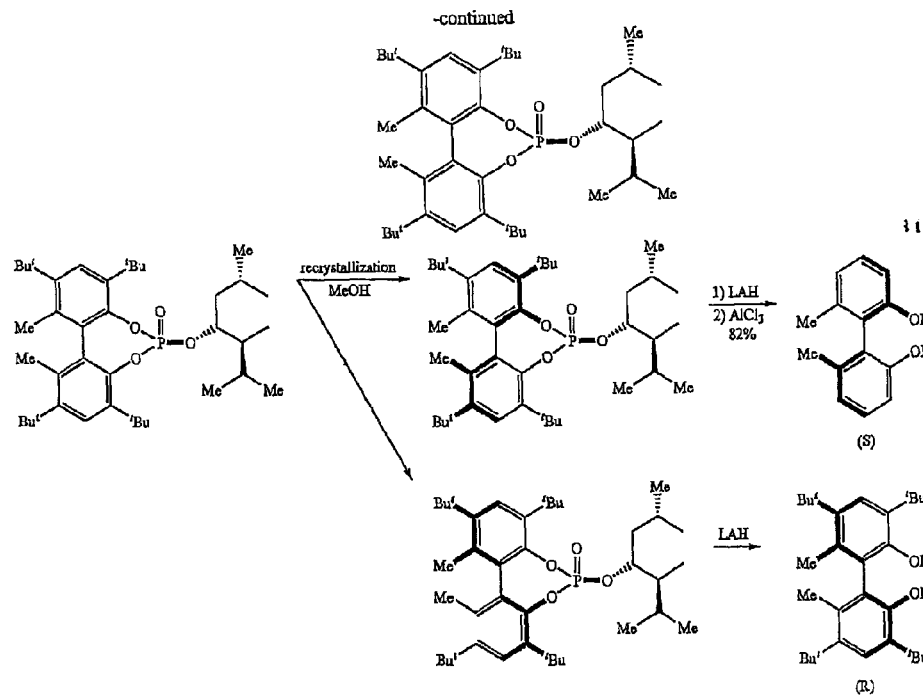

" Should read

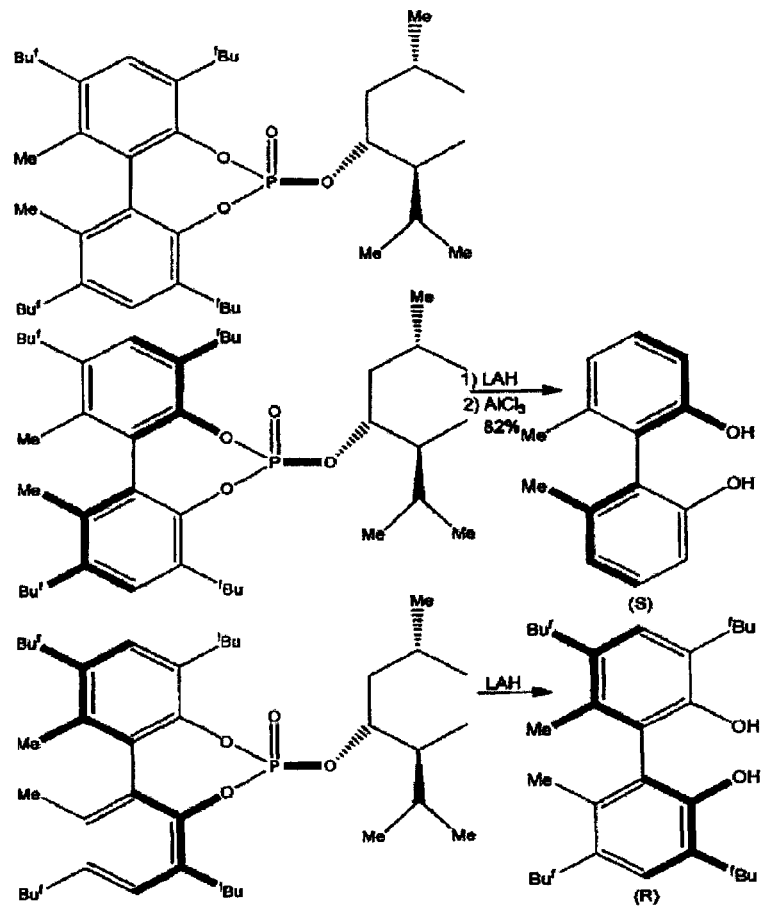

"

UNITED STATES PATENT AND TRADEMARK OFFICE
CERTIFICATE OF CORRECTION

PATENT NO.       : 8,110,680 B2
APPLICATION NO.  : 12/443588
DATED            : February 7, 2012
INVENTOR(S)      : Keiji Maruoka et al.

It is certified that error appears in the above-identified patent and that said Letters Patent is hereby corrected as shown below:

Under Columns 23 & 24, lines 52-65, please delete;

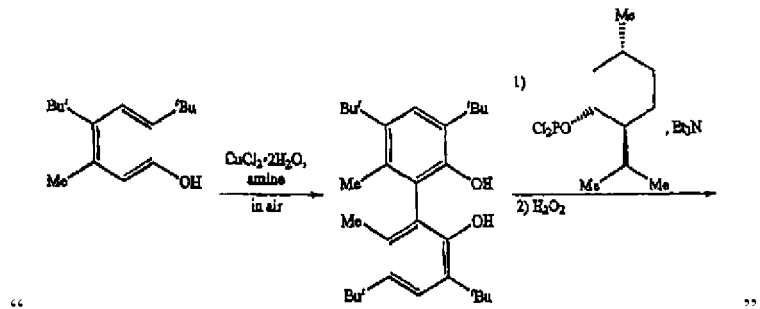

"             "

Should read

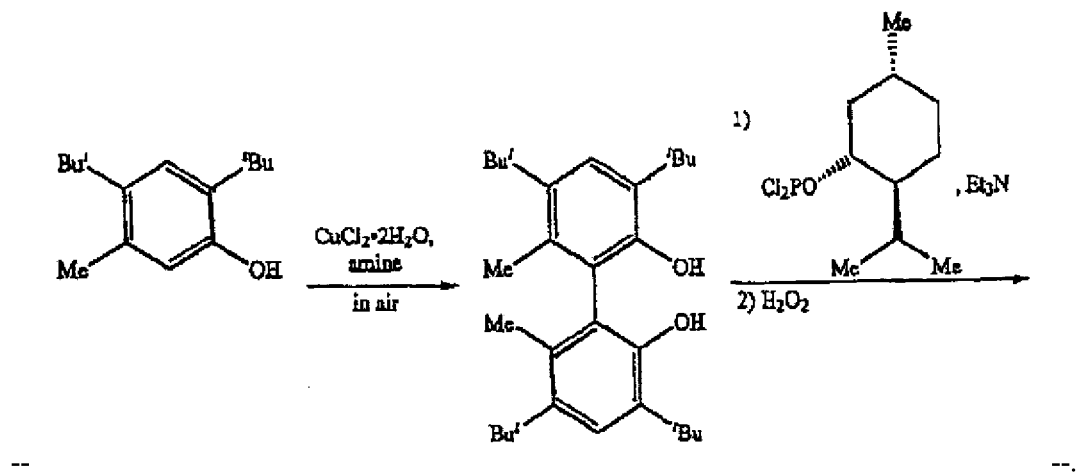

--             --.

This certificate supersedes the Certificate of Correction issued June 26, 2012.

Signed and Sealed this
Twenty-fifth Day of September, 2012

David J. Kappos
*Director of the United States Patent and Trademark Office*

CERTIFICATE OF CORRECTION (continued)
U.S. Pat. No. 8,110,680 B2

Page 2 of 2

Columns 25 & 26 under -continued, lines 1-32, please delete;

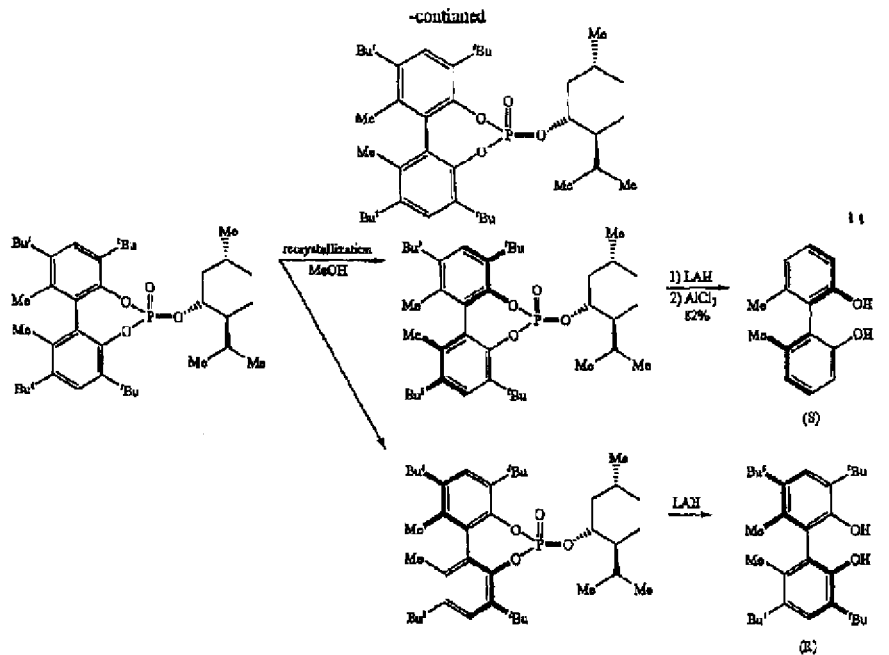

"

Should read

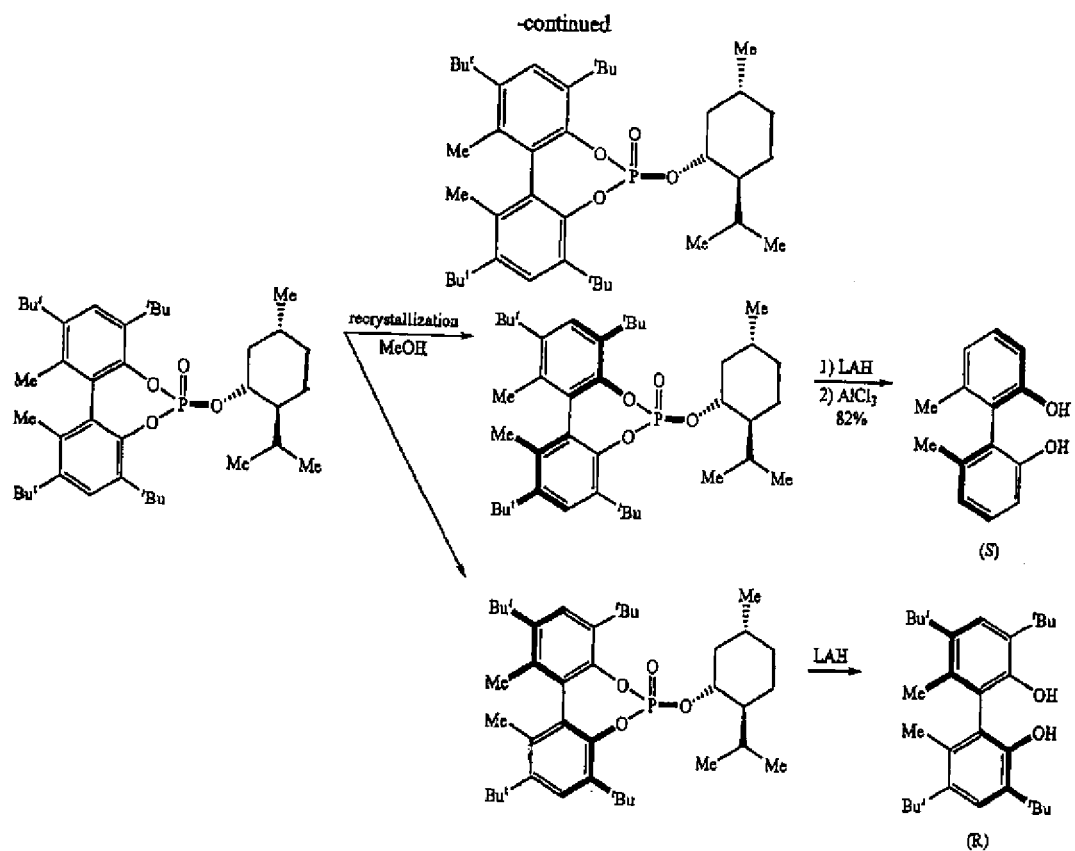

--            --.